US012607758B2

(12) United States Patent
    Riehl

(10) Patent No.: US 12,607,758 B2
(45) Date of Patent: Apr. 21, 2026

(54) DELTA MODULATED BASELINE RESTORATION FOR PHOTON COUNTING COMPUTED TOMOGRAPHY

(71) Applicant: Analog Devices, Inc., Wilmington, MA (US)

(72) Inventor: Patrick Riehl, Wilmington, MA (US)

(73) Assignee: Analog Devices, Inc., Wilmington, MA (US)

( * ) Notice: Subject to any disclaimer, the term of this patent is extended or adjusted under 35 U.S.C. 154(b) by 284 days.

(21) Appl. No.: 18/027,009

(22) PCT Filed: Aug. 6, 2021

(86) PCT No.: PCT/US2021/044866
    § 371 (c)(1),
    (2) Date: Mar. 17, 2023

(87) PCT Pub. No.: WO2022/060483
    PCT Pub. Date: Mar. 24, 2022

(65) Prior Publication Data
    US 2023/0367025 A1      Nov. 16, 2023

Related U.S. Application Data

(60) Provisional application No. 63/080,315, filed on Sep. 18, 2020.

(51) Int. Cl.
    *G01T 1/24*       (2006.01)
    *A61B 6/00*       (2024.01)
        (Continued)

(52) U.S. Cl.
    CPC .............. *G01T 1/247* (2013.01); *A61B 6/032* (2013.01); *A61B 6/4241* (2013.01); *A61B 6/5205* (2013.01); *G01N 23/046* (2013.01)

(58) Field of Classification Search
    CPC .... H04N 25/773; H04N 5/325; G01N 23/046; G01N 23/083; A61B 6/4241;
        (Continued)

(56) References Cited

U.S. PATENT DOCUMENTS

| 2010/0181491 A1 | 7/2010 | Karim et al. |
| 2016/0203620 A1 | 7/2016 | Zou et al. |

(Continued)

FOREIGN PATENT DOCUMENTS

| CN | 105793734 A | 7/2016 |
| CN | 101606846 A | 12/2019 |

(Continued)

OTHER PUBLICATIONS

International Search Report and Written Opinion for International Patent Application No. PCT/US2021/044866, mailed Mar. 11, 2021 (11 pages).

(Continued)

*Primary Examiner* — Irakli Kiknadze
(74) *Attorney, Agent, or Firm* — ArentFox Schiff LLP

(57)      ABSTRACT

One embodiment is a baseline restoration ("BLR") circuit for a photo-counting computed tomography ("PCCT") signal chain, the BLR circuit comprising a comparator for comparing a shaper voltage output from a shaper component of the PCCT signal chain with a baseline voltage, the comparator outputting a single bit indicative of whether the shaper voltage is above or below the baseline voltage; a low pass filter connected to filter a voltage signal output from the comparator; and a transconductor connected to receive a filtered voltage signal output from the low pass filter, convert the filtered voltage signal to a current signal, and feed the current signal back to an input of the PCCT signal chain.

20 Claims, 15 Drawing Sheets

(51) Int. Cl.
| | |
|---|---|
| *A61B 6/03* | (2006.01) |
| *A61B 6/42* | (2024.01) |
| *G01N 23/046* | (2018.01) |

(58) Field of Classification Search
CPC ......... A61B 6/032; A61B 6/5205; A61B 6/54;
A61B 6/58; G01T 1/247; G01T 1/17;
G01T 1/2985; G01T 1/2928; G01T 1/241;
G01T 1/249; G01T 1/24; H03G 3/30;
H03M 1/1245; H03M 1/361; H03M
1/002; H03M 1/1014; H03M 1/1215;
H03M 1/1009; H03M 1/34; H03M 1/52;
H03M 1/06; H03M 1/0641; H03M
1/0673; H03M 1/164; G01J 1/44; G01J
2001/444; H03L 7/0891; H03L 7/093;
G11B 20/10037; G11B 20/10046; G11B
20/10194; G11B 20/10203; G11B
20/1037; G11B 20/10509; G11B
2220/2516
USPC ................................................... 378/4, 5, 19
See application file for complete search history.

(56) References Cited

U.S. PATENT DOCUMENTS

| | | | |
|---|---|---|---|
| 2016/0377745 | A1 | 12/2016 | Daerr et al. |
| 2017/0322319 | A1* | 11/2017 | Iniewski ................... G01T 1/24 |
| 2018/0217278 | A1 | 8/2018 | O'Neill et al. |
| 2018/0321395 | A1* | 11/2018 | Steadman Booker .. G01T 1/244 |
| 2021/0063589 | A1* | 3/2021 | Iniewski ................. G01T 7/005 |

FOREIGN PATENT DOCUMENTS

| | | |
|---|---|---|
| JP | S6021474 A | 2/1985 |
| JP | 2020-38185 A | 3/2020 |

OTHER PUBLICATIONS

Gustavsson et al., "A High-Rate Energy-Resolving Photon-Counting ASIC for Spectral Computed Tomography," IEEE Transactions on Nuclear Science—IEEE Trans Nucl Sci. 59. 30-39. 10.1109/TNS.2011.2169811 (2012).

Cao et al., "Pulse neutron logging instrument front-end signal processing circuit", vol. 40, Issue 1, Feb. 20, 2016 (English Abstract Submitted).

* cited by examiner

DELTA MODULATED BASELINE RESTORATION FOR PHOTON COUNTING COMPUTED TOMOGRAPHY

RELATED APPLICATIONS

This application is a 35 U.S.C. § 371 National Phase of International Patent Application No. PCT/US2021/044866, filed Aug. 6, 2021, which claims priority to U.S. Provisional Patent Application No. 63/080,315, entitled "DELTA MODULATED BASELINE RESTORATION FOR PHOTON COUNTING COMPUTED TOMOGRAPHY" and filed Sep. 18, 2020, the contents of which applications are hereby incorporated herein by reference in their entireties.

FIELD OF THE DISCLOSURE

This disclosure relates generally to the field of photon counting computed tomography (PCCT) and, more particularly, to a delta modulated baseline restoration (BLR) technique for PCCT.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DETAILED DESCRIPTION OF EXAMPLE EMBODIMENTS

Figure 1:
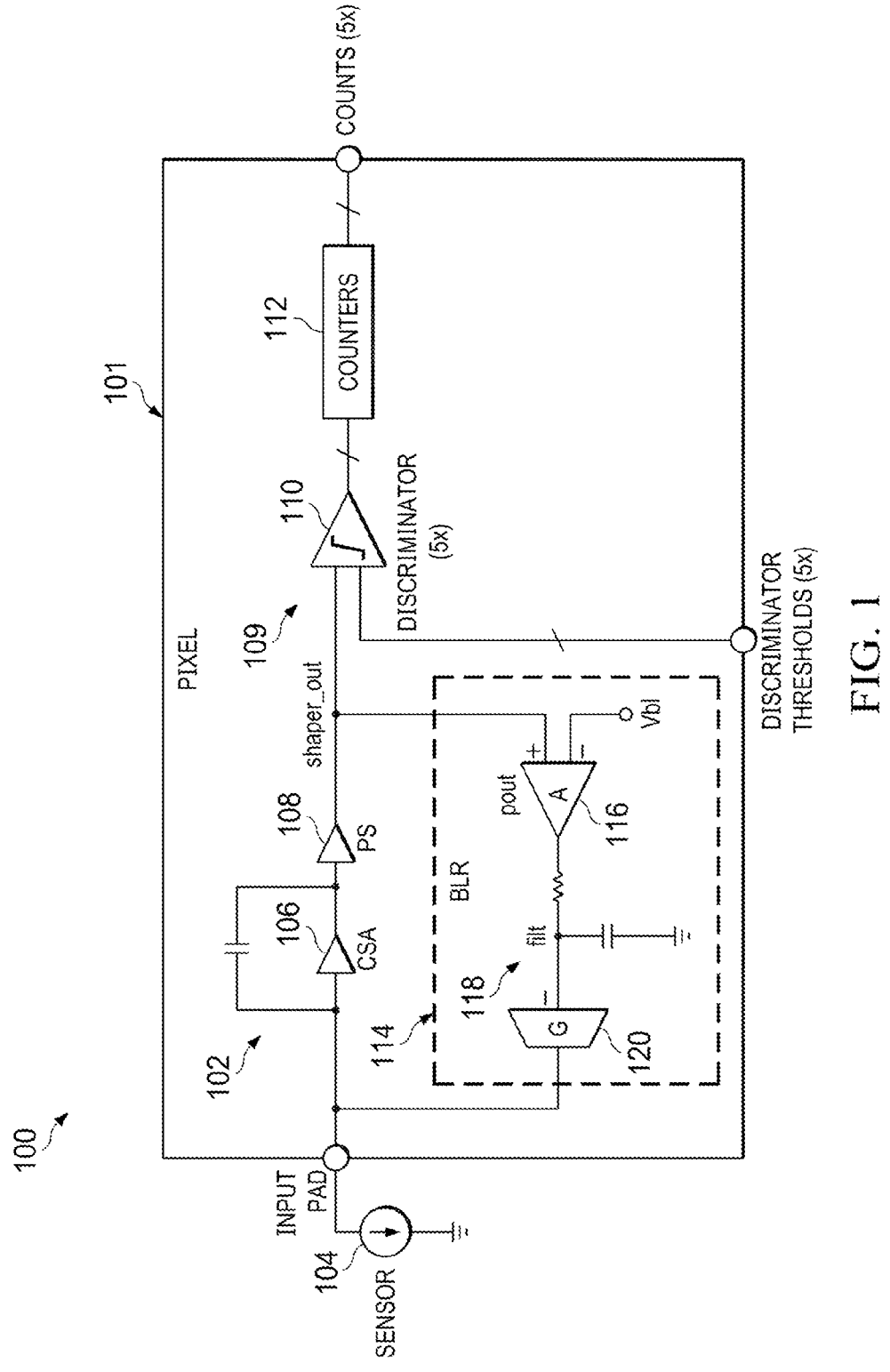
FIG. 1 is a schematic block diagram of a typical PCCT signal chain including a linear BLR circuit in accordance with features of certain embodiments described herein.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C). The term "between," when used with reference to measurement ranges, is inclusive of the ends of the measurement ranges. When used herein, the notation "A/B/C" means (A), (B), and/or (C).

The description uses the phrases "in an embodiment" or "in embodiments," which may each refer to one or more of the same or different embodiments. Furthermore, the terms "comprising," "including," "having," and the like, as used with respect to embodiments of the present disclosure, are synonymous. The disclosure may use perspective-based descriptions such as "above," "below," "top," "bottom," and "side"; such descriptions are used to facilitate the discussion and are not intended to restrict the application of disclosed embodiments. The accompanying drawings are not necessarily drawn to scale. Unless otherwise specified, the use of the ordinal adjectives "first," "second," and "third," etc., to describe a common object, merely indicate that different instances of like objects are being referred to and are not intended to imply that the objects so described must be in a given sequence, either temporally, spatially, in ranking or in any other manner.

In the following detailed description, reference is made to the accompanying drawings that form a part hereof, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense.

The following disclosure describes various illustrative embodiments and examples for implementing the features and functionality of the present disclosure. While particular components, arrangements, and/or features are described below in connection with various example embodiments, these are merely examples used to simplify the present disclosure and are not intended to be limiting. It will of course be appreciated that in the development of any actual embodiment, numerous implementation-specific decisions must be made to achieve the developer's specific goals, including compliance with system, business, and/or legal constraints, which may vary from one implementation to another. Moreover, it will be appreciated that, while such a development effort might be complex and time-consuming; it would nevertheless be a routine undertaking for those of ordinary skill in the art having the benefit of this disclosure.

In the Specification, reference may be made to the spatial relationships between various components and to the spatial orientation of various aspects of components as depicted in the attached drawings. However, as will be recognized by those skilled in the art after a complete reading of the present disclosure, the devices, components, members, apparatuses, etc. described herein may be positioned in any desired orientation. Thus, the use of terms such as "above", "below", "upper", "lower", "top", "bottom", or other similar terms to describe a spatial relationship between various components or to describe the spatial orientation of aspects of such components, should be understood to describe a relative relationship between the components or a spatial orientation of aspects of such components, respectively, as the components described herein may be oriented in any desired direction. When used to describe a range of dimensions or other characteristics (e.g., time, pressure, temperature, length, width, etc.) of an element, operations, and/or conditions, the phrase "between X and Y" represents a range that includes X and Y.

Further, the present disclosure may repeat reference numerals and/or letters in the various examples. This repetition is for the purpose of simplicity and clarity and does not in itself dictate a relationship between the various embodiments and/or configurations discussed. Example embodiments that may be used to implement the features and functionality of this disclosure will now be described with more particular reference to the accompanying FIGURES.

In a traditional computed tomography (CT) scanning system, X-rays are generated by an X-ray source, passed through an object of interest, and transformed by a collimator into light that is captured by a detector implemented as a photodiode arrays. The photodiode arrays transform the light into analog electrical signals, which are converted into digital signals using an analog-to-digital (A/D) converter. The digital signal output from the A/D converter is used to produce a gray scale image referred to as a CT scan.

Photon-counting CT (PCCT) imaging is relatively new technique that may offer significant advantages and improvements over existing CT imaging techniques such as described above. A photon-counting CT system employs a photon-counting detector (PCD) comprising a semiconductor layer for implementing an array of detector pixels that register the interactions of individual photons with the PCD. By tracking the deposited energy of each interaction, detector pixels of a PCD record an approximate energy spectrum as well as an intensity of the photons, such that photon-counting CT is a spectral, or energy-resolved, CT technique.

In contrast, traditional CT scanners use energy-integrating detectors (EIDs) in which the total energy from one or more photons as well as electronic noise deposited in a pixel during a fixed period of time is registered. EIDs therefore register only photon intensity, analogous to black-and-white photography. In contrast, PCDs register both photon intensity and spectral information, analogous to color photography.

Photon-counting CT imaging turns the three-step process described above into a more streamlined direct conversion from X-ray to charge via semiconductor layer comprising the PCD. In particular, the semiconductor material used to implement the PCD efficiently turns each X-ray photon into a burst of charge that is proportional to the energy of the X-ray. Benefits of this technology include improved signal-to-noise, reduced X-ray dose to the patient due to the higher resolution that may be achieved with the same X-ray dose, improved spatial resolution and, through use of several "energy bins," the ability to distinguish multiple contrast agents and multiple types of materials/tissues.

When a photon interacts in a PCD, the height of a resulting electrical pulse is approximately proportional to the energy of the photon. By comparing each pulse produced in a pixel with a suitable low-energy threshold, contributions from low-energy events (resulting from both photon interactions and electronic noise) can be filtered out. As a result, PCDs have higher signal-to-noise and contrast-to-noise ratios as compared to EIDs, enabling an increase in image quality at the same X-ray exposure level or a decrease in patient X-ray dose with the same image quality.

Introduction of more energy thresholds above the low-energy threshold enables a PCD to be divided into several discrete energy bins. Each registered photon is assigned to a specific bin depending on its energy, such that each pixel measures a histogram of the incident X-ray spectrum. This spectral information enables a qualitative determination of the material composition of each pixel in the reconstructed CT image, as opposed to the estimated average linear attenuation coefficient obtained in a conventional CT scan. Additionally, using more than two energy bins enables discrimination between dense bones and calcifications versus heavier elements commonly used as contrast agents, reducing the need for a reference scan before contrast injection and thereby further reducing the amount of X-ray dose to which a patient is subjected.

FIG. 1 is a schematic block diagram of an example signal processing architecture for a PCCT system 100. The system 100 comprises a photon counting detector (PCD) including a number of detector pixels, represented in FIG. 1 by a detector pixel 101. A forward signal path 102 from a sensor 104 includes a charge-sensitive amplifier (CSA) 106 and a pulse shaper (PS) 108, followed by counting circuitry 109 including a set of N discriminators 110 and counters 112. In operation, X-rays impinging on the sensor 104 cause current pulses (or charge packets) to be injected to the forward signal path 102, which converts them to voltage pulses at the inputs of the discriminators 110. In particular, the current pulses are amplified by the CSA 106 and shaped by PS 108 before being output as voltage pulses to the discriminators 110. The discriminators 110 quantize the current pulses according to their energy, which quantized pulses are in turn counted by the counters 112. In certain embodiments, the N discriminators (or comparators) 110 respectively compare the pulses to N increasing voltage thresholds. The set of discriminators 110 create pulsed digital outputs in a "thermometer code." The pulses may be counted at each level, or threshold, by counters 112, with the resulting count values representing how many X-ray hits at each of the N thresholds have occurred. It will be recognized that the thresholds are set to match the different voltages corresponding to the different energy photons.

It will be recognized that the sensor 102 includes a significant component of slowly varying leakage current. Left uncompensated for, this leakage current would pass through the forward signal chain and produce an offset at inputs of the discriminators 110, distorting the measured spectrum. To counter this effect, a baseline restorer (BLR) 114 is provided in the system 100. The BLR 114 creates a slow negative feedback loop around the CSA 106 and PS 108 that regulates the long-term value of the PS output to some desired voltage by injecting a slowly varying current at the CSA 106 input. This BLR circuit 114 uses an initial linear voltage gain stage 116 referenced to the desired baseline voltage $V_{bl}$. The voltage gain stage 116 is followed by a low-pass filter 118 and finally a transconductor 120. If implemented with linear circuits, the BLR 114 will regulate the average shaper output voltage (shaper_out). If flux rates are low, meaning that the input signal current due to X-ray flux is small compared to the leakage current, this is equivalent to regulating the baseline voltage of the shaper 108 output.

In contrast, if flux rates are high, meaning that the input signal current due to X-ray flux is significant compared to the leakage current, an issue commonly referred to as "undershoot" may occur. In particular, in response to high flux rate conditions, the BLR 114 will successfully cancel the leakage current; however, the baseline of the shaper output voltage will be significantly less than the baseline voltage $(V_{bl})$ due to the fact that the average stimulus current $I_{stim}$ will include a significant contribution from the input signal current. The BLR circuit 114 has no way to distinguish leakage current from input signal current, so it effectively cancels both. The resulting measured spectrum includes a shift to lower energies, as each charge pulse (if it can be distinguished from others) starts from a lowered baseline.

Figure 2:
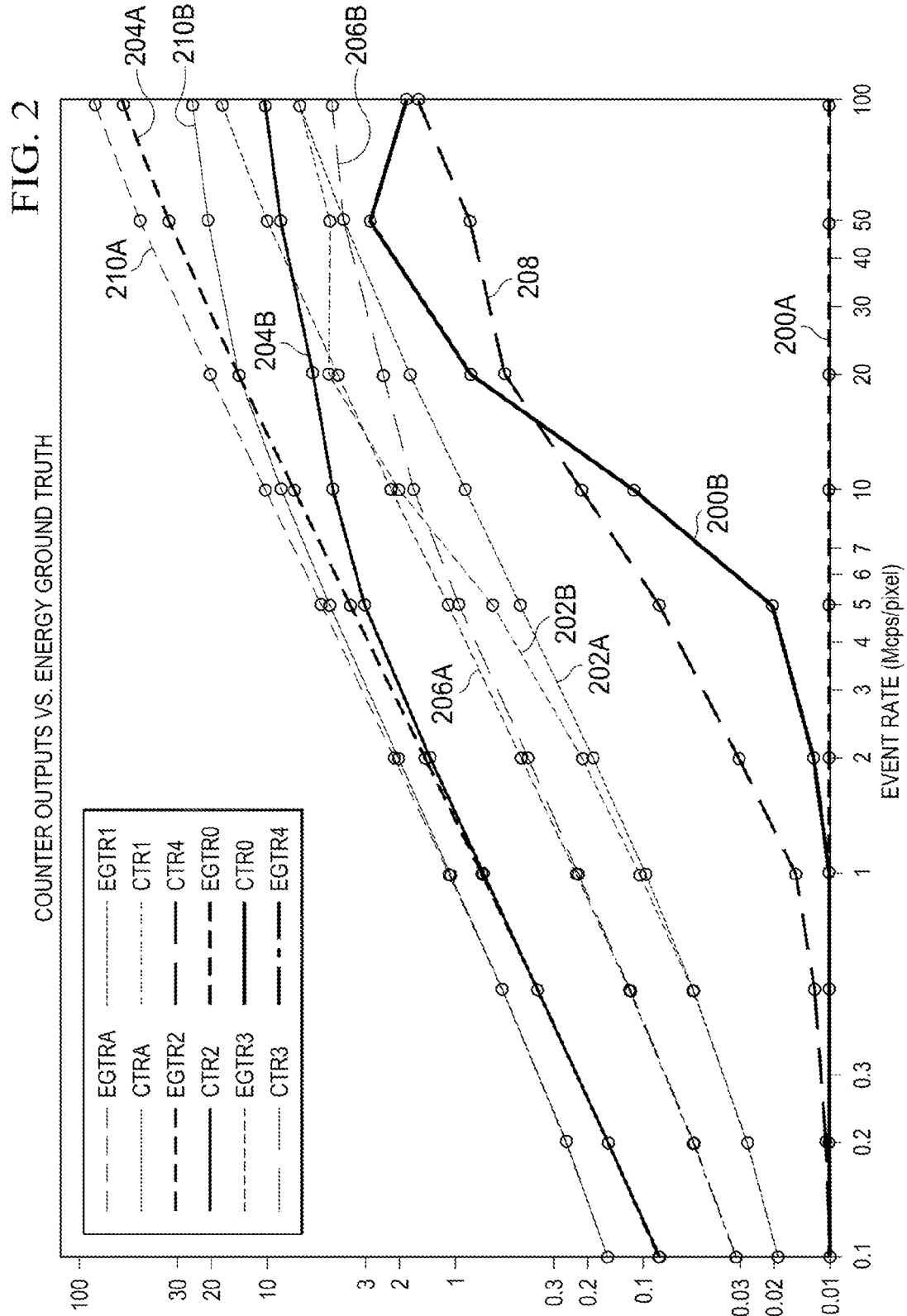
FIG. 2 is a plot illustrating example counting curves for the PCCT signal chain of FIG. 1 with linear BLR enabled in accordance with features of certain embodiments described herein.

The effect of undershoot can be observed in FIG. 2, which shows a plot illustrating actual generated events per bin (i.e., "energy ground truth" or "EGT") versus counter outputs for each of five counter bins for an example frame of PCCT data. As shown in the example illustrated in FIG. 2, waveforms 200A and 200B respectively correspond to EGT and counter output for bin 0. Waveforms 202A and 202B respectively correspond to EGT and counter output for bin 1. Waveforms 204A and 204B respectively correspond to EGT and counter output for bin 2. Waveforms 206A and 206B respectively corresponds to EGT and counter output for bin 3. A single waveform 208 corresponds to both EGT and counter output for bin 4. Waveforms 210A and 210B respectively correspond to total EGT and counter output for all bins. An increase in counts of approximately 10-20 mega counts per second (Mcps) relative to the ground truth may be observed in bins 0 and 1, serving as evidence that undershoot causes higher energy events to be miscounted in lower energy bins.

In general, BLR is sufficiently effective in canceling leakage currents that there is a negligible difference between counting results with 50 nA leakage current and counting results with a 0 nA leakage current, with the undershoot effect being effectively the same for both cases.

Table 1 below illustrates the effectiveness of BLR in cancelling leakage currents as well as the undershoot problem. Each column in Table 1 represents a simulation of a single frame at a high flux (30 Mcps) at a different delay time in μs after a step change from zero flux. In other words, each column effectively represents the same sequence of X-rays superimposed on a different leakage current from near zero to 30 nA. The change across columns of Table 1 is minimal, indicating that the leakage current cancellation has been successful. Without BLR, there would be a heavy shift in counts towards higher bins with increasing delay; however, it may be observed that there is significant spectral shift towards lower bins in all columns due to the overshoot effect.

TABLE 1

| | | Delay (us) | | | | |
|---|---|---|---|---|---|---|
| | | 0 | 25000 | 50000 | 75000 | 100000 |
| Bin 4 | GT | 0 | 0 | 0 | 0 | 0 |
| | CT | 225 | 225 | 225 | 225 | 225 |
| Bin 3 | GT | 907 | 907 | 907 | 907 | 907 |
| | CT | 296 | 296 | 296 | 296 | 296 |
| Bin 2 | GT | 1767 | 1767 | 1767 | 1767 | 1767 |
| | CT | 458 | 458 | 460 | 460 | 460 |
| Bin 1 | GT | 294 | 294 | 294 | 294 | 294 |
| | CT | 564 | 563 | 562 | 562 | 562 |
| Bin 0 | GT | 0 | 0 | 0 | 0 | 0 |
| | CT | 139 | 139 | 139 | 139 | 140 |
| Total | GT | 2968 | 2968 | 2968 | 2968 | 2968 |
| | CT | 1682 | 1681 | 1682 | 1682 | 1683 |

Figure 3:
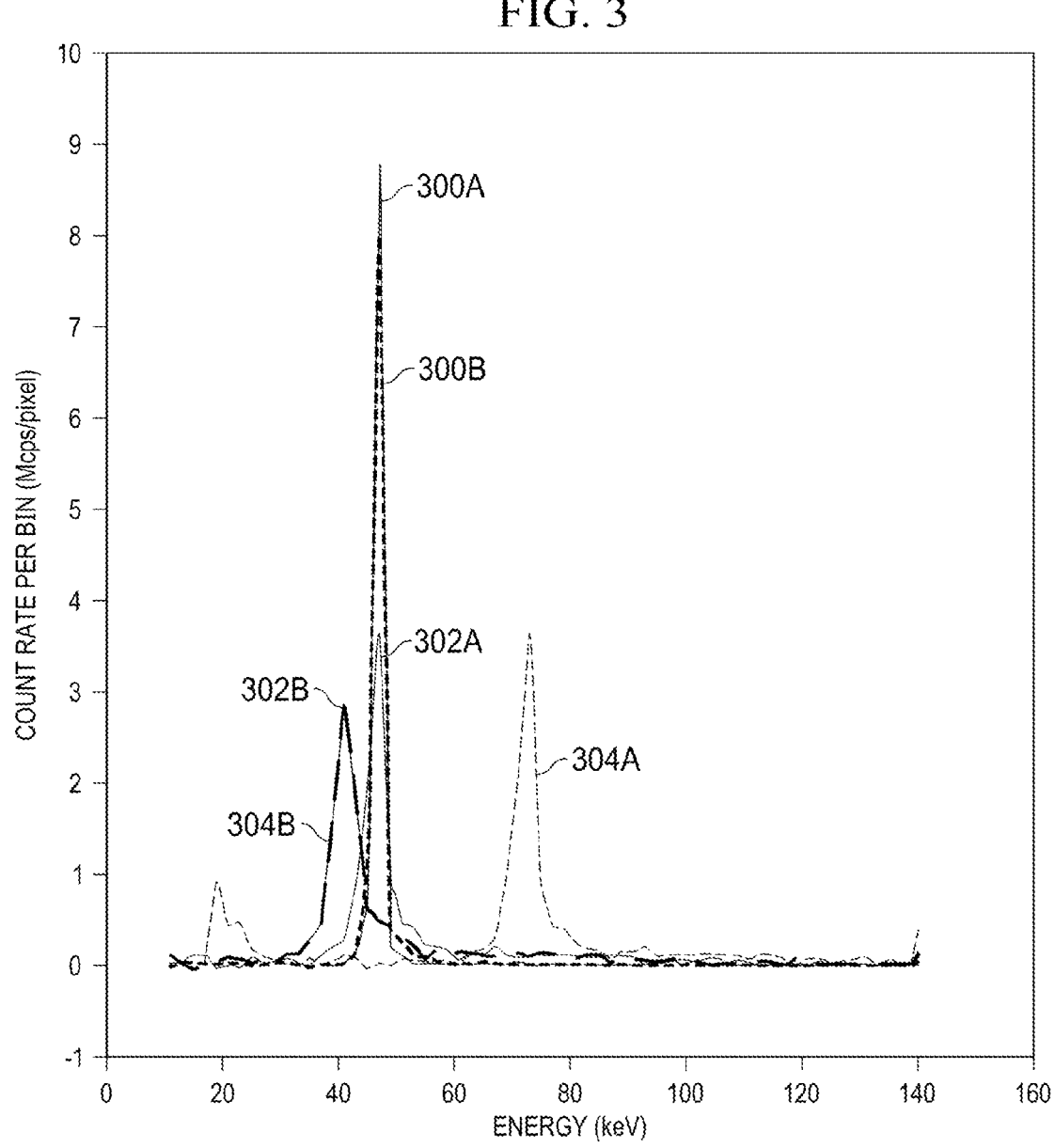
FIG. 3 is a graph illustrating an example undershoot effect of the linear BLR of the PCCT of FIG. 1 in accordance with features of certain embodiments described herein.

Referring now to FIG. 3, waveforms shown therein illustrate the results of another experiment demonstrating the BLR undershoot effect. In particular, the waveforms shown in FIG. 3 are the result of a series of example simulations carried out with a superposition of a 10 Mcps, 50 kiloelectron volt (keV) periodic tone with a realistic spectrum at varying flux rates. The output spectrum was captured using a threshold sweep. The spectrum flux was maintained at a low level to render the tone clearly visible in the output spectrum.

Waveform 300A represents the observed tone at 1 nA flux with BLR off. In contrast, waveform 300B represents the observed tone at 1 nA flux with BLR on. As evident from a visual comparison of waveforms 300A and 300B, at 1 nA flux, there is no observable difference in the spectrum whether the BLR is on (waveform 300B) or off (waveform 300A). Waveform 302A represents the observed tone at 10 nA flux with BLR off. In contrast, waveform 302B represents the observed tone at 10 nA flux with BLR on. As evident from a visual comparison of waveforms 302A and 302B, a shift to lower energy occurs in the observed tone when the BLR is on. The observed tone does not shift at 10 nA flux with the BLR off. Waveform 304A represents the observed tone at 10 nA flux and 50 nA leakage current with the BLR off. In contrast, waveform 304B represents the observed tone at 10 nA flux and 50 nA leakage current with the BLR on and is coincident with the waveform 302B. As illustrated in FIG. 3 by a comparison of waveforms 304A and 304B, once a leakage current is applied, the energy spectrum of the observed tone shifts dramatically higher with the BLR off, while it remains at the same energy level with BLR on. This result is summarized in Table 2 below.

TABLE 2

| | 0 nA leakage | 50 nA leakage |
|---|---|---|
| BLR off | 47 keV | 73 keV |
| BLR on | 41 keV | 41 keV |

Although undershoot is undesirable, the benefits of using a BLR to cancel leakage current heavily outweigh the costs. The undershoot effect is a response to flux changes, which are deterministic. There is an opportunity to correct for this in post-processing. The leakage current can vary over many frames even as flux remains constant. Moreover, the leakage current may vary from pixel to pixel or with aging or temperature of the sensor. Accordingly, it is much more important to cancel the leakage current than to avoid the undershoot effect. Use of a BLR loop is desirable, therefore, and the BLR loop must have sufficient loop gain to cancel most of the leakage current.

Figure 4:
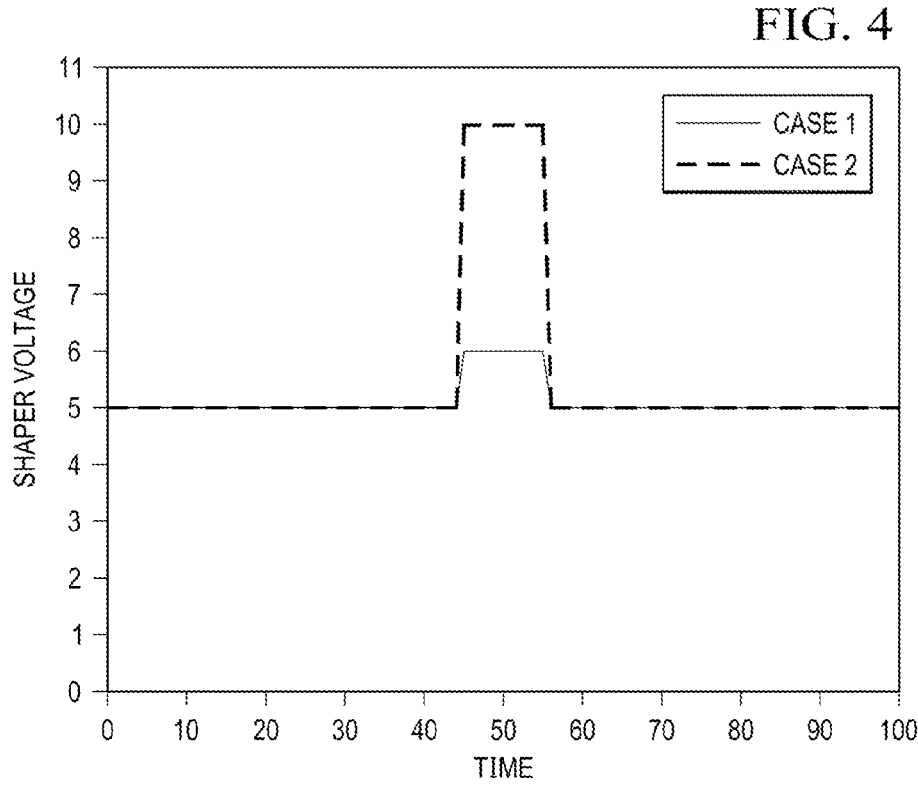
FIG. 4 is a graph illustrating idealized shaper voltages with different peak heights in accordance with features of certain embodiments described herein.
Figure 5:
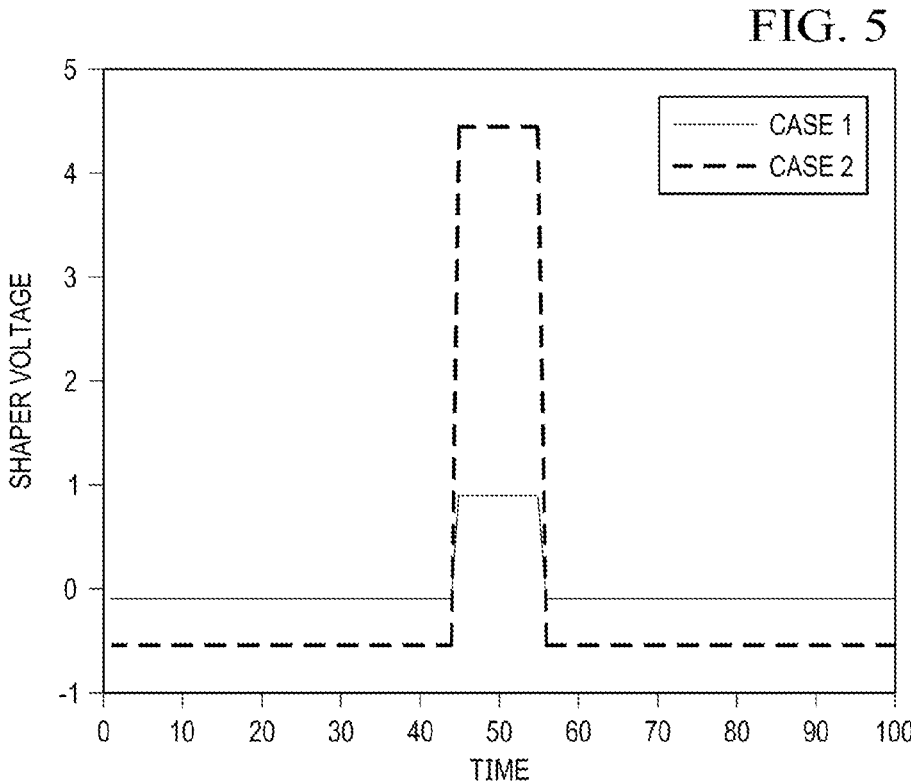
FIG. 5 is a graph illustrating idealized shaper voltages with different peak heights after application of linear BLR in accordance with features of certain embodiments described herein.

It can be demonstrated that undershoot is unavoidable in linear BLR circuits, but nonlinear feedback may be used to improve undershoot somewhat. Consider an idealized example shown in FIG. 4, which illustrates shaper voltages without BLR for two events (case 1 and case 2, respectively) having the same baseline voltage and timing, but different peak energies. If a linear BLR method is applied in an attempt to restore the baseline voltage to zero, the shaper voltages illustrated in FIG. 5 are obtained. Undershoot is much worse for case 2 than case 1 because the event contributes more to the average value; however, the BLR circuit could simply truncate the event in case 2 to look like case 1. This suggests that a nonlinear gain function could be effective at reducing undershoot.

Figure 6:
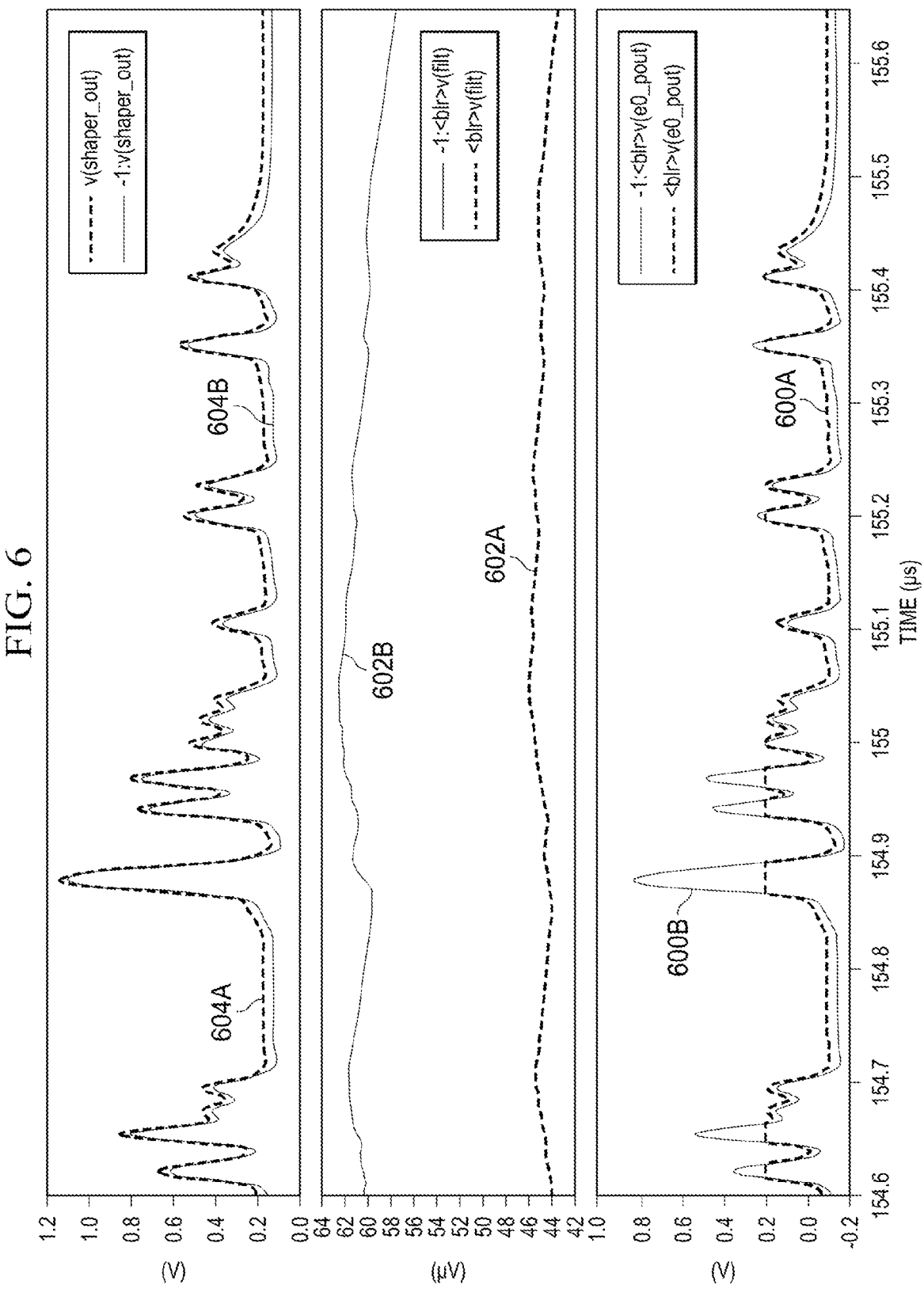
FIG. 6 is a graph illustrating waveforms for linear and slew-rate limited BLR methods in accordance with features of certain embodiments described herein.

In accordance with features of a prior art embodiment, a BLR circuit may include a slew-rate limiter that inhibits the feedback from responding to large positive pulses. This method may reduce undershoot. A slew-rate limited BLR circuit may be implemented by simply modifying a linear BLR to include a limiter on the output of the initial gain stage. FIG. 6 illustrates operation of an example slew-rate limited BLR with a stimulus flux of 18.75 Mcps. Waveforms 600A and 600B (<blr>v(e0_pout) and −1:<blr>v(e0_pout)) correspond to the output of the initial voltage gain stage in a circuit employing a non-slew-rate limited BLR and a circuit employing a slew-rate limited BLR, respectively. In waveform 600B, which represents the slew-rate limited variant (−1:<blr>v(e0_pout)), the charge events are truncated to 0.2V. Waveforms 602A and 602B ((<blr>v(filt) and −1:<blr>v(filt)) represent the internal voltage after the integrator in a circuit employing a non-slew-rate limited BLR and a circuit employing a slew-rate limited BLR, respectively. Waveforms 604A and 604B (v(shaper_out) and −1:v (shaper_out)) represent the shaper voltage in a circuit employing a non-slew-rate limited BLR and a circuit employing a slew-rate limited BLR, respectively. As illustrated in FIG. 6, undershoot is reduced by the slew-rate limited version of the BLR. It can be demonstrated that the response to leakage currents is equivalent to the linear BLR.

Figure 7:
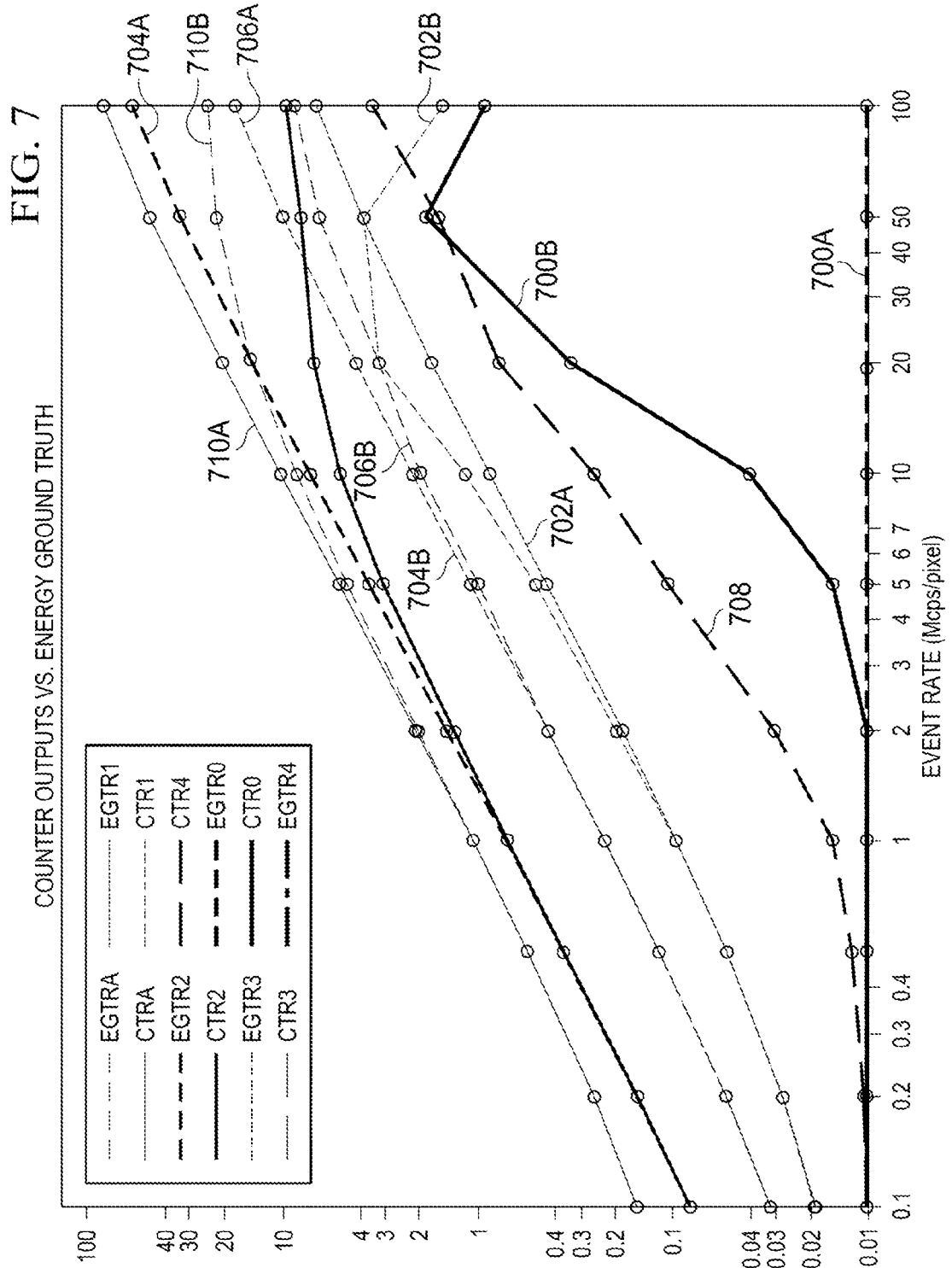
FIG. 7 is a graph illustrating example counting curves for a PCCT signal chain implementing a slew-rate limited BLR in accordance with features of certain embodiments described herein.

FIG. 7 shows a plot illustrating actual generated events per bin (i.e., "energy ground truth" or "EGT") versus counter outputs for each of five counter bins for the same example frame of PCCT data of FIG. 2 using a slew-rate limited BLR. As shown in the example illustrated in FIG. 7, waveforms 700A and 700B respectively correspond to EGT and counter output for bin 0. Waveforms 702A and 702B respectively correspond to EGT and counter output for bin 1. Waveforms 704A and 704B respectively correspond to EGT and counter output for bin 2. Waveforms 706A and 706B respectively corresponds to EGT and counter output for bin 3. A single waveform 708 corresponds to both EGT and counter output for bin 4. Waveforms 710A and 710B respectively correspond to total EGT and counter output for all bins. As is evidenced by a comparison of the plot shown in FIG. 7 with the plot shown in FIG. 2, the reduction in undershoot enabled by the slew-rate limited BLR improves the counting curves' correspondence to ground truth; however, a significant increase in counts relative to the ground truth may still be observed in bins 0 and 1.

It is apparent from the example described above with reference to the slew rate limited BLR that limiting the range of the feedback can provide some rejection of signal currents. As such, a feedback loop with infinite gain before the integrator but limited range would be equivalent to replacing the initial gain stage with a comparator plus one-bit DAC. A delta pulse width modulator (delta PWM) or simply delta modulator produces an output that tracks an input with 1-bit feedback; such a modulator is only concerned with whether the output is above or below the input. The result is a nonlinear gain function when the loop is out of regulation, which may be beneficial for embodiments described herein.

Figure 8:
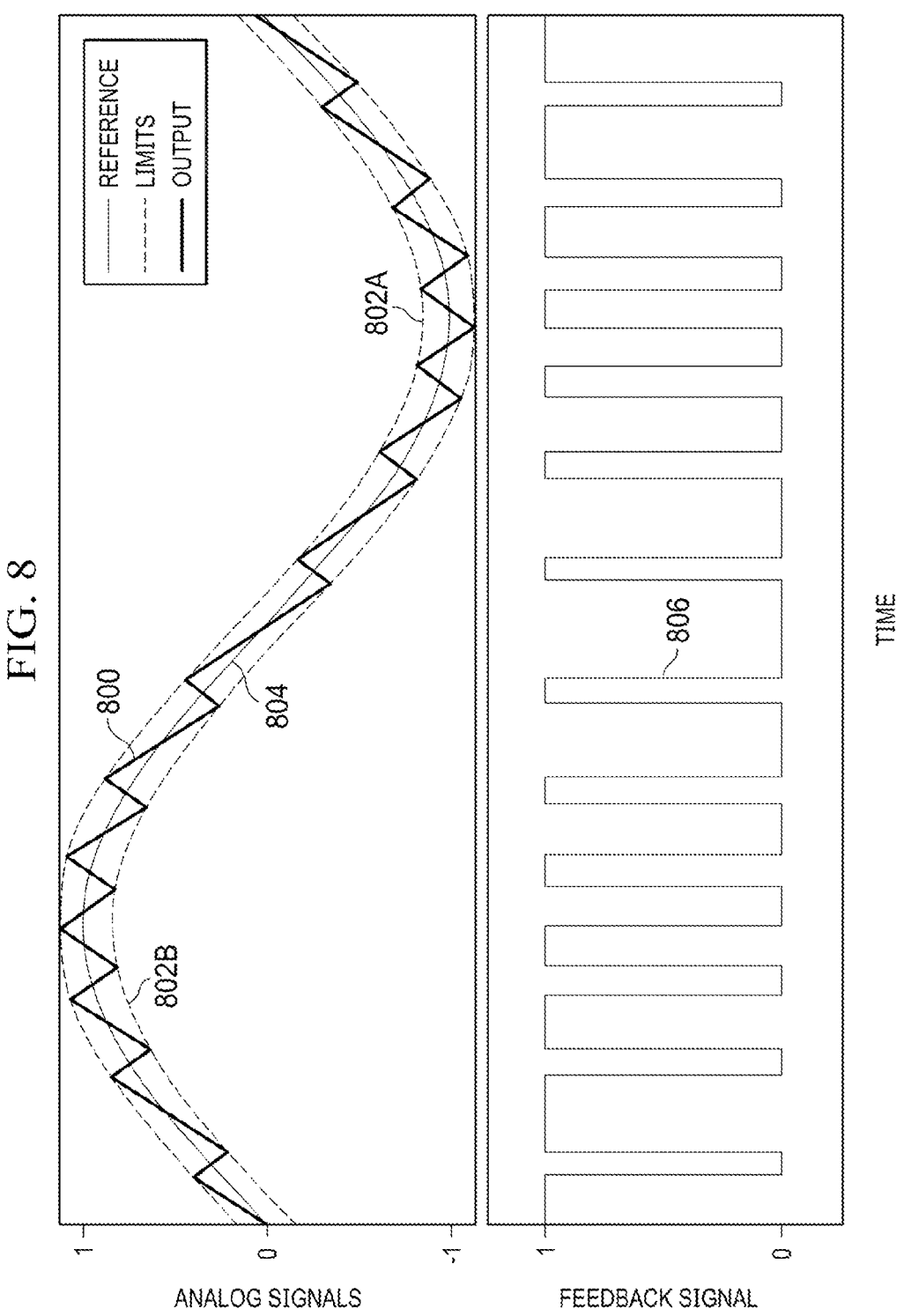
FIG. 8 is a graph illustrating operational principles of a delta pulse width modulator in accordance with features of certain embodiments described herein.

FIG. 8 illustrates operational principles of a delta modulator. As shown in FIG. 8, an analog output signal 800 is compared with upper and lower limits 802A, 802B, which correspond to a reference signal 804 offset by a given value. Each time the output signal 800 reaches one of the limits 802A, 802B, the delta modulator changes state, as represented by a waveform 806.

Figure 9:
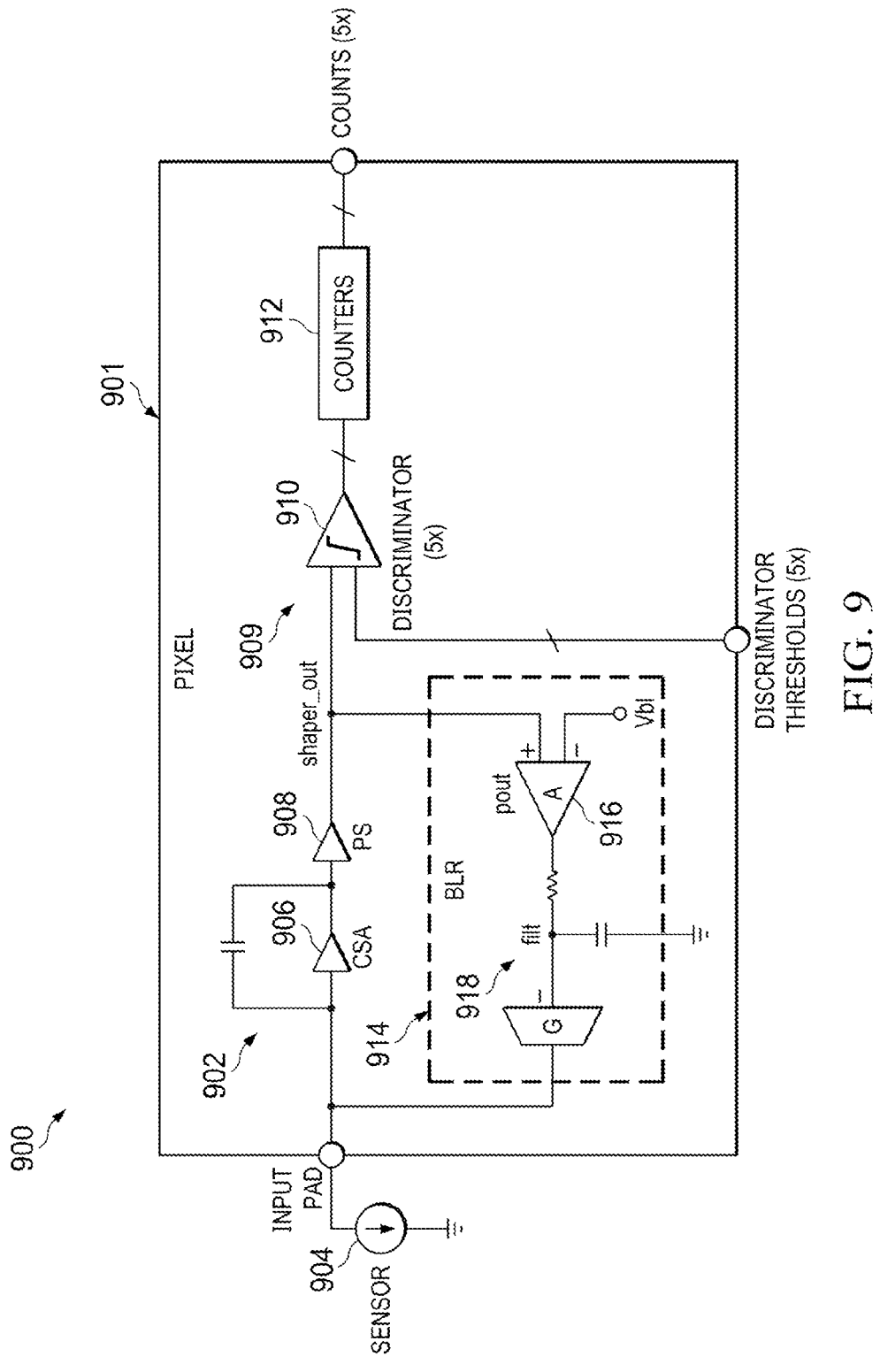
FIG. 9 is a schematic block diagram of a PCCT signal chain including a delta-modulated BLR circuit in accordance with features of certain embodiments described herein.

The BLR loop 114 of the circuit 100 (FIG. 1) can be modified to behave like a delta modulator by replacing the linear gain stage 116 with a comparator. In this configuration, the low-pass filter acts as an integrator in a delta modulator. FIG. 9 illustrates a schematic block diagram of an example signal processing architecture for a PCCT system 900 having a BLR loop modified to act as a delta modulator in accordance with features of embodiments described herein. The system 900 comprises a photon counting detector (PCD) including a number of detector pixels, represented in FIG. 9 by a detector pixel 901. A forward signal path 902 from a sensor 904 includes a CSA 906 and a PS 908, followed by a counting circuitry 909 including a set of N discriminators 910 and counters 912. In operation, X-rays emitted from an X-ray source, traveling through an object of interest, and impinging on the sensor 904 cause current pukes (or charge packets) to be injected to the forward signal path 902, which converts them to voltage pulses at the inputs of the discriminators 910. In particular, the current pulses are amplified by the CSA 906 and shaped by PS 908 before being output as voltage pulses to the discriminators 910. The discriminators 910 quantize the current pulses according to their energy, which quantized pulses are in turn counted by the counters 912. In certain embodiments, the N discriminators (or comparators) 910 respectively compare the pulses to N increasing voltage thresholds. The set of discriminators 910 create pulsed digital outputs in a "thermometer code." The pulses may be counted at each level, or threshold, by counters 912, with the resulting count values representing how many X-ray hits at each of the N thresholds have occurred. It will be recognized that the thresholds are set to match the different voltages corresponding to the different energy photons.

For reasons described in detail above, a BLR 914 is provided in the system 900. The BLR 914 creates a slow negative feedback loop around the CSA 906 and PS 908 that regulates the long-term value of the PS output to some desired voltage by injecting a slowly varying current at the CSA 906 input. This BLR circuit 914 is a delta modulated BLR circuit in accordance with features of embodiments described herein. As such, instead of a linear voltage gain stage 116 (FIG. 1), the BLR 914 includes a comparator 916 referenced to the desired baseline voltage $V_{bl}$. The comparator 916 is followed by a low-pass filter 918 and finally a transconductor 920. In this configuration, the low-pass filter acts 918 as an integrator of a delta modulator.

Figure 10:
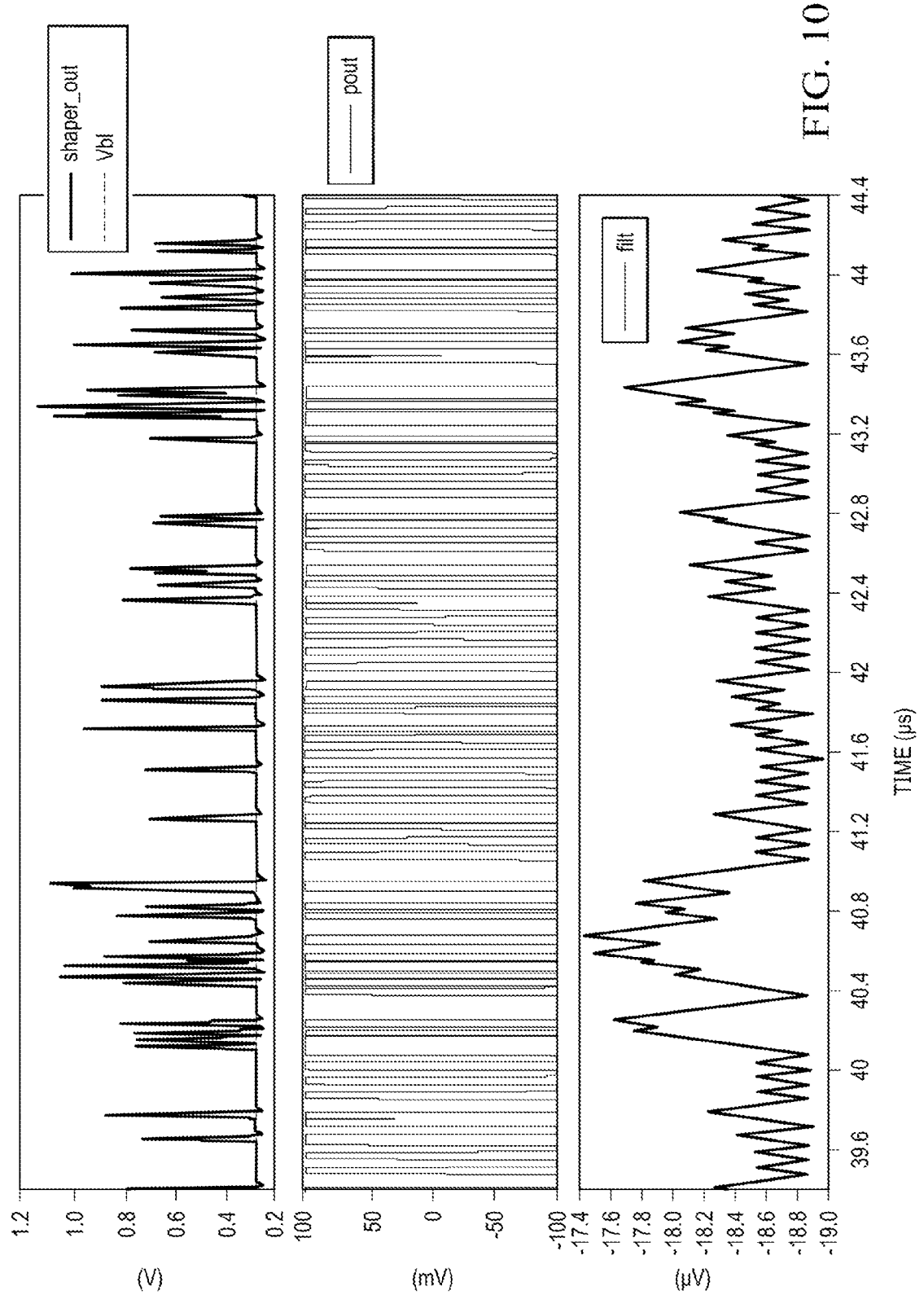
FIG. 10 is a graph illustrating internal waveforms of the delta-modulated BLR of FIG. 9 in accordance with features of certain embodiments described herein.

The behavioral simulation described above with reference to the linear BLR may be modified to use such a delta-modulated BLR with the same time constant as the original linear BLR. FIG. 10 illustrates internal waveforms of a delta-modulated BLR such as shown in FIG. 9 in accordance with features of embodiments described herein. A comparison between a shaper output (shaper_out) 1000 and a baseline set point (vbl) 1002 produces 1-bit feedback (pout) 1004 (node pout in FIG. 9). The feedback voltage pout is integrated to produce a filter voltage (filt) 1006. The feedback current is linearly proportional to the integrated voltage.

Figure 11:
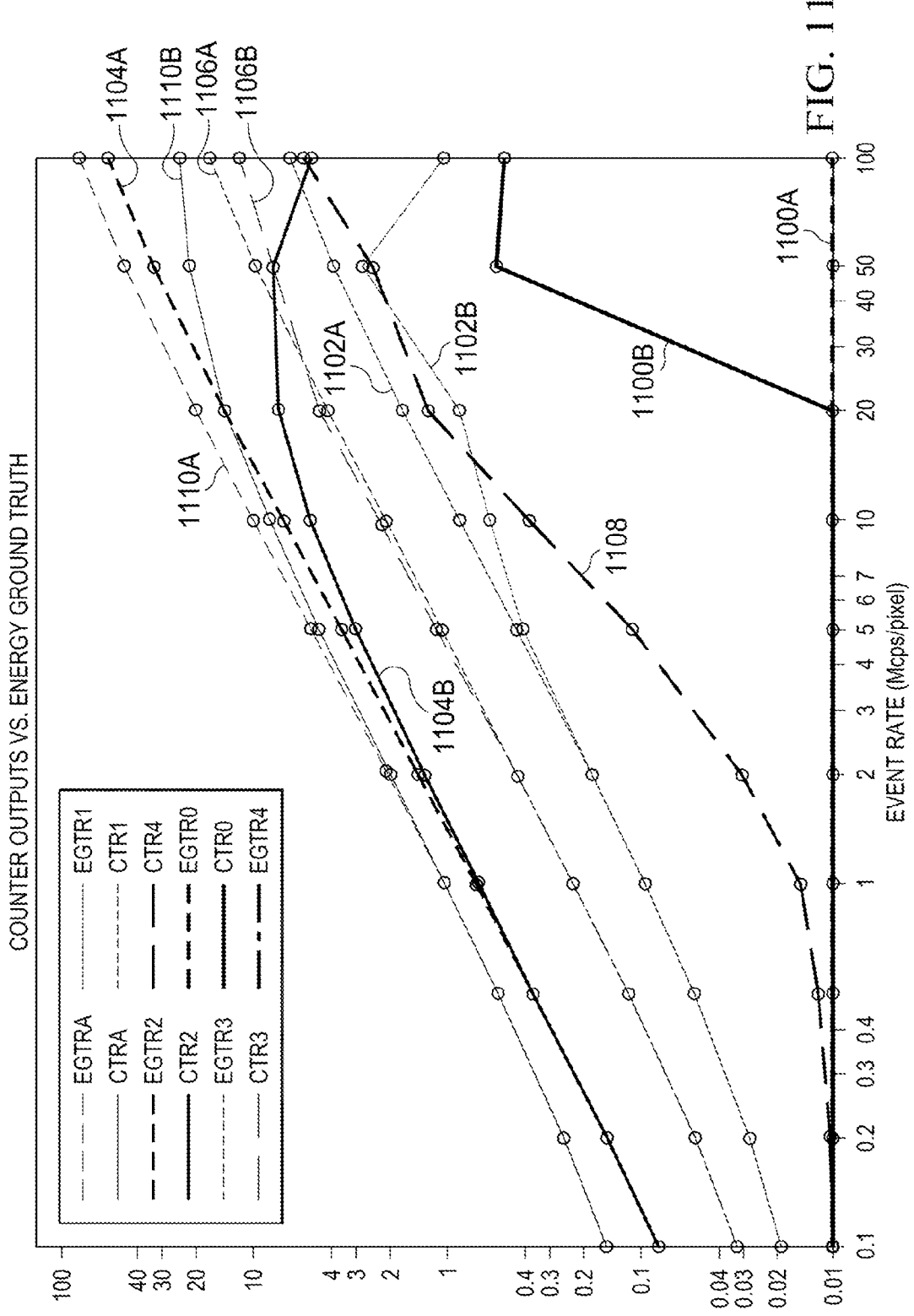
FIG. 11 is a graph illustrating example counting curves for the PCCT signal chain of FIG. 9 with nonlinear BLR enabled in accordance with features of certain embodiments described herein.

FIG. 11 shows a plot of counting curves illustrating actual generated events per bin (i.e., "energy ground truth" or "EGT") versus counter outputs for each of five counter bins for the same example frame of PCCT data of FIGS. 2 and 7 using a delta modulated BLR, such as shown in FIG. 9. As shown in the example illustrated in FIG. 11, waveforms 1100A and 1100B respectively correspond to EGT and counter output for bin 0. Waveforms 1102A and 1102B respectively correspond to EGT and counter output for bin 1. Waveforms 1104A and 104B respectively correspond to EGT and counter output for bin 2. Waveforms 1106A and 1106B respectively corresponds to EGT and counter output for bin 3. A single waveform 1108 corresponds to both EGT and counter output for bin 4. Waveforms 1110A and 1110B respectively correspond to total EGT and counter output for all bins. As is evidenced by a comparison of the plot shown in FIG. 11 with the plots shown in FIGS. 2 and 7, the reduction in undershoot enabled by the slew-rate limited BLR improves the counting curves' correspondence to ground truth. In particular, it will be noted that the performance in medium-to-high flux for the delta modulated BLR is notably better than the corresponding linear BLR and the slew-rate limited BLR.

It will be recognized that there are two practical problems with a KR circuit implemented on an IC. One is that the offset of the CMOS amplifier will itself contribute to baseline variation and drift, as it defines the virtual ground of the system. The second is that the passive components (resistor or current source and capacitor) needed to define the BLR low-pass pole may be exceptionally large when implemented on chip. The delta-modulated BLR circuit described herein provides a solution to both problems.

A clocked circuit can be implemented to slow down the time constant without increasing the size of the on-chip passives. Once the BLR circuit is clocked, chopper stabilization can be applied to null out the offset of the input comparator. Alternatively, an auto-zero function can be applied to null out the offset of the input comparator. It will be noted that it is difficult to apply these techniques to a linear BLR circuit without introducing glitches or noise at the comparator input.

Figure 12A:
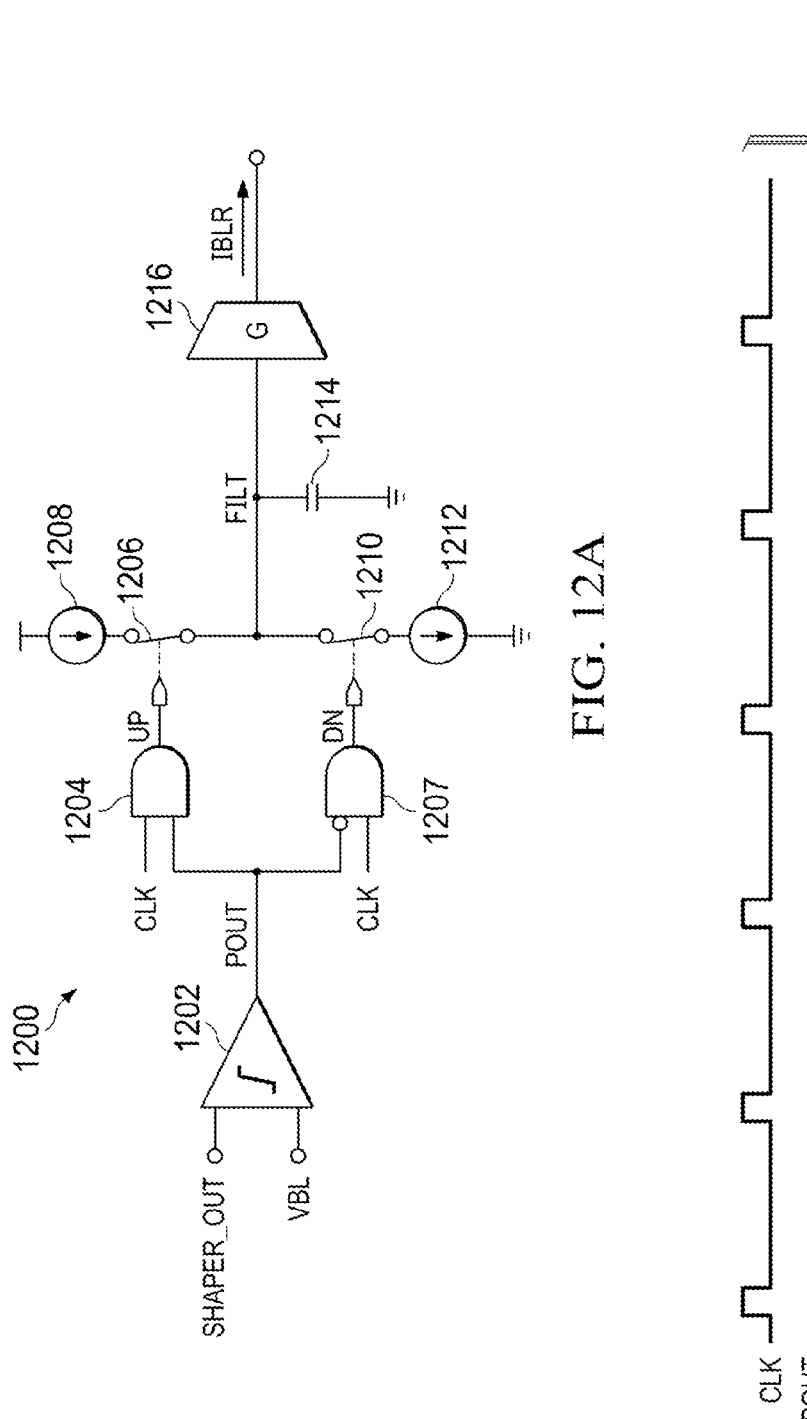
FIG. 12A is a schematic block diagram for a delta-modulated BLR circuit employing clocked time constant reduction and chopper stabilization in accordance with features of certain embodiments described herein.

FIG. 12A illustrates a schematic block diagram of a clocked BLR circuit 1200 in accordance with features of embodiments described herein. The comparator 1202 generates a digital signal POUT according to the result of a comparison of the input signals SHAPER_OUT and VBL. The signal POUT is processed using an AND gate 1204 along with a clock signal CLK to produce a signal UP. This signal is asserted with the same timing as the CLK signal when the feedback circuit indicates that IBLR should be increased to bring SHAPER_OUT closer to VBL. Generating a pulse on the UP signal causes the switch 1206 to turn on for a period of time. This in turn causes a pulse of current from the current source 1208 to be conducted to the filter capacitor 1214. The pulse of current causes the voltage FILT to increment by an amount determined by the pulse timing and value of current source 1208. Similarly, the inverse of POUT is processed using an AND gate 1207 along with CLK to produce a signal DN. This signal is asserted with the same timing as the CLK signal when the feedback circuit indicates that IBLR should be decreased to bring SHAPER-_OUT closer to VBL. Generating a pulse on the DN signal causes the switch 1210 to turn on for a period of time. This in turn causes a pulse of current from the current source 1212 to be conducted to the filter capacitor 1214. The pulse of current causes the voltage FILT to decrement by an amount determined by the pulse timing and value of current source 1208.

Figure 12B:
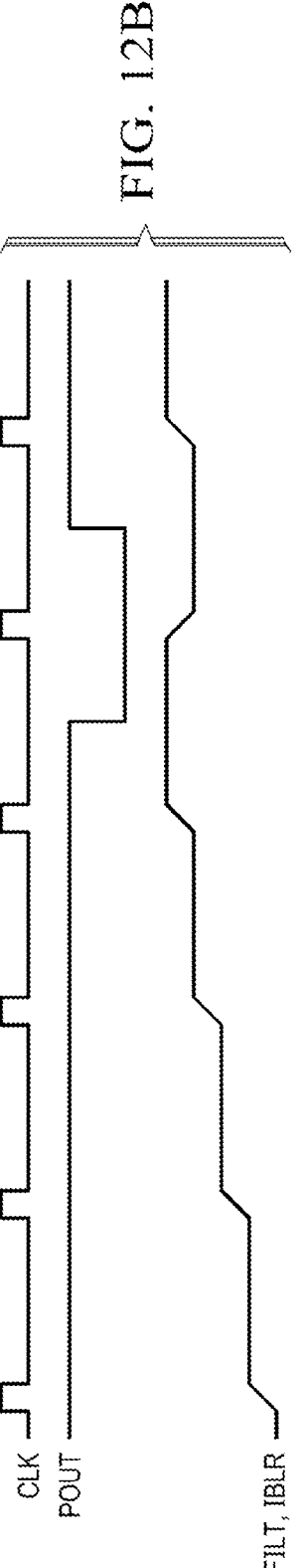
FIG. 12B illustrates a timing diagram of critical waveforms of the delta-modulated BLR circuit of FIG. 12A in accordance with features of certain embodiments described herein.

FIG. 12B illustrates a timing diagram for critical waveforms of the KR circuit 1200 as shown in FIG. 12A. Current is only integrated on the capacitor for a duty cycle defined by CLK, which allows the use of a smaller capacitor to achieve the same time constant. Since the comparator only needs to sample once per CLK pulse, the dead time can be used to implement chopper stabilization controlled by a signal $\phi$.

Figures 13A, 13B:
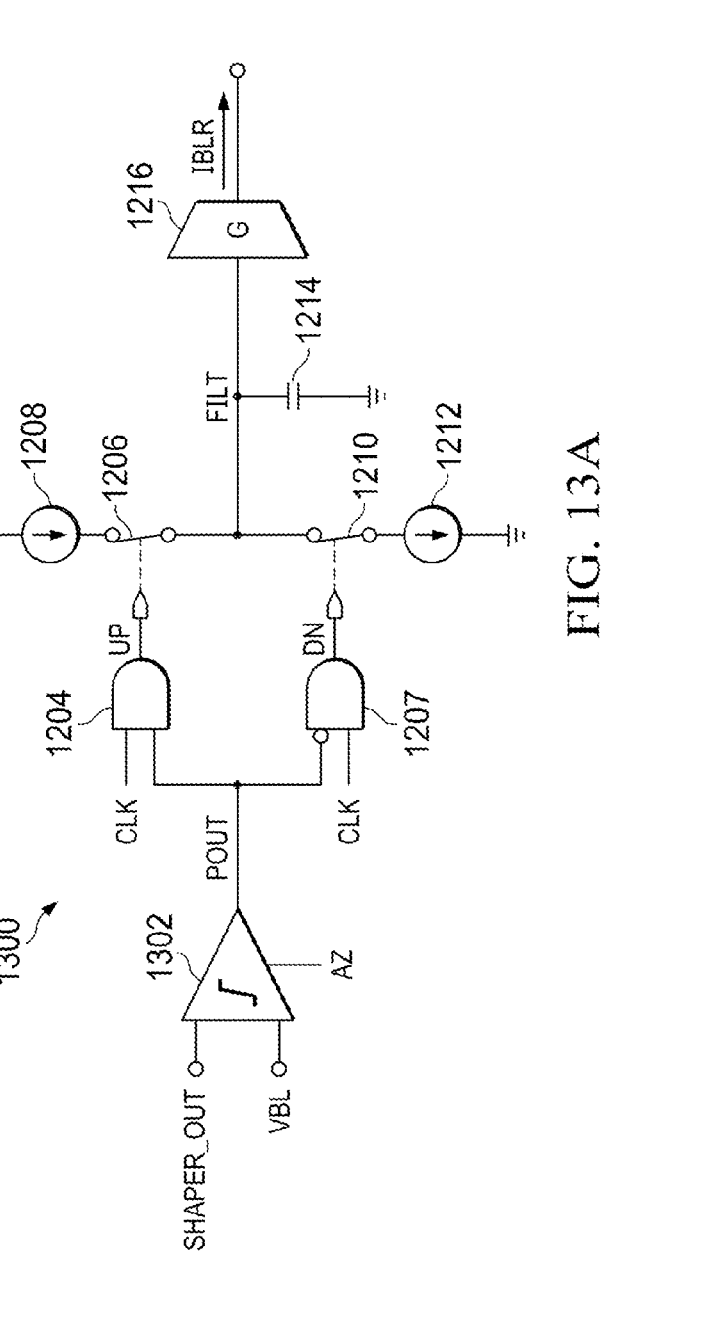
FIG. 13A illustrates a schematic block diagram of a delta-modulated BLR circuit that includes an auto-zero capability in accordance with features of embodiments described herein.
FIG. 13B illustrates a timing diagram of critical waveforms of the delta-modulated BLR circuit of FIG. 13A in accordance with features of certain embodiments described herein.

FIG. 13A illustrates a schematic block diagram of a delta-modulated BLR circuit 1300 that includes an auto-zero capability in accordance with features of embodiments described herein. An auto-zero capability allows a comparator or amplifier 1302 to use a first auto-zero phase to periodically measure its own offset and store that offset so as to cancel its effect during a second measurement phase. Many examples of auto-zero functions for comparators and amplifiers are commonly known. In order to use an auto-zero function for the delta-modulated BLR circuit, a second timing signal AZ is generated. AZ is asserted during periods where CLK is not asserted. Thus, during the time periods in which the output of the comparator would otherwise be ignored, the comparator offset can be calibrated out. Note that these unused time periods are not available in a conventional, linear BLR. FIG. 13B illustrates a timing diagram for critical waveforms of the BLR circuit 1300 as shown in FIG. 13A.

Figures 14A, 14B:
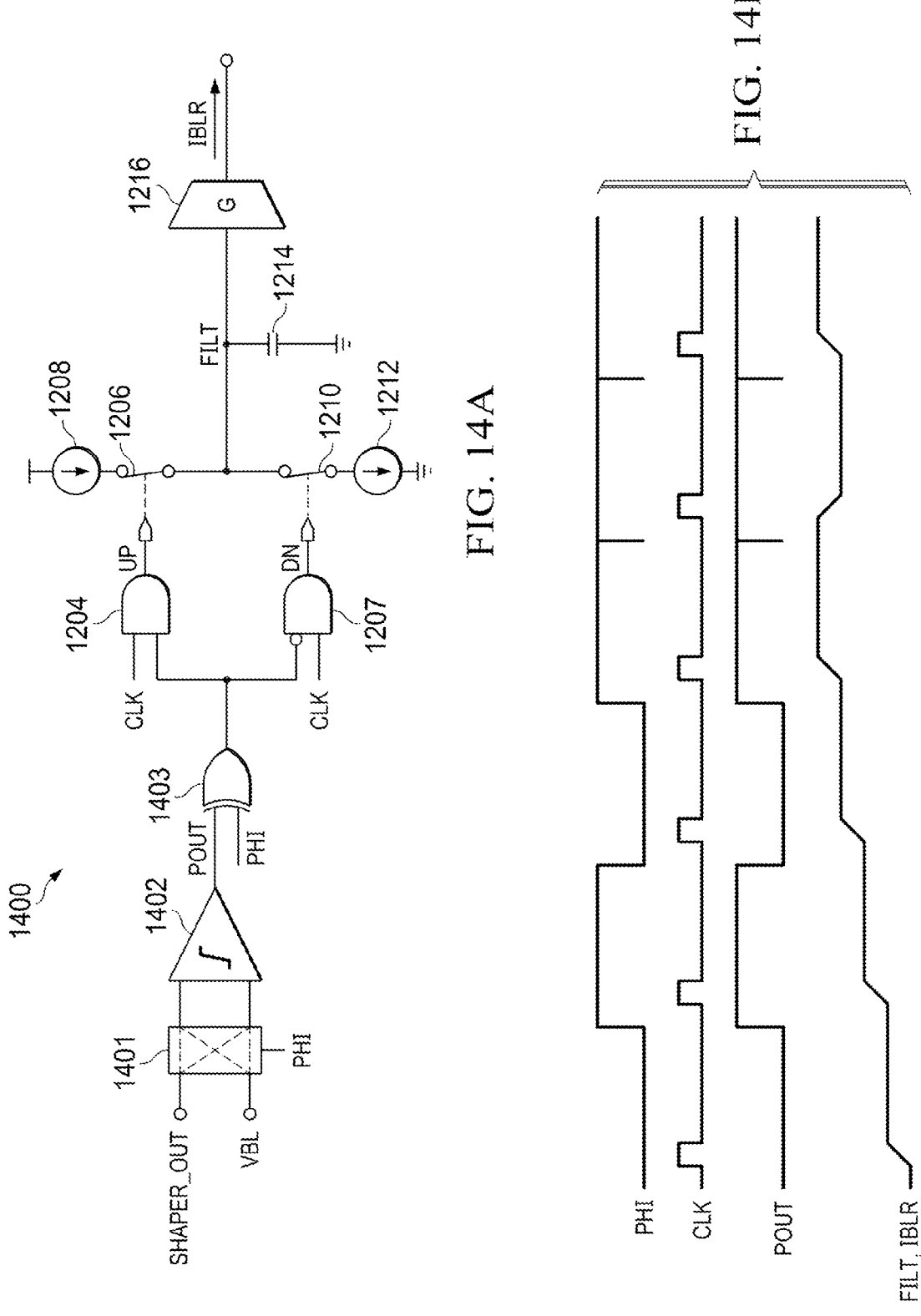
FIG. 14A illustrates a schematic block diagram of a delta-modulated BLR circuit that includes chopper stabilization in accordance with features of embodiments described herein.
FIG. 14B illustrates a timing diagram of critical waveforms of the delta-modulated BLR circuit of FIG. 14A in accordance with features of certain embodiments described herein.

FIG. 14A illustrates a schematic block diagram of a delta-modulated BLR circuit 1400 that includes chopper stabilization in accordance with features of embodiments described herein. Chopper stabilization is a technique used to cancel out the offsets of amplifiers. In a conventional chopper stabilization scheme, an input signal is first inverted, then applied to an amplifier. The output of the amplifier is again inverted and passed through a low-pass filter that rejects signals at the chopper frequency. For signals applied to the amplifier, the two inversions cancel out and have no theoretical effect. But offsets in the amplifier are modulated to the chopper frequency and removed by the low-pass filter. Thus the chopper-stabilized amplifier may appear as if it has no offset. To implement a chopper stabilization scheme for the delta-modulated BLR, a chopper signal PHI with a period twice that of CLK is generated. Input signals SHAPER_OUT and VBL are applied to a crosspoint switch 1401 which passes them straight through to a comparator 1403 for a first digital value of PHI and crisscrosses them for a second digital value of PHI. An output POUT of the comparator 1402 and PHI are applied to an XOR gate 1403, which inverts the output signal. The result of the comparison thus has no DC contribution from the comparator offset. Note that a linear BLR circuit does not offer the opportunity to activate the crosspoint switch 1401 and XOR gate 1403 without potentially introducing glitches and/or artifacts on the BLR output signal IBLR. FIG. 14B illustrates a timing diagram for critical waveforms of the BLR circuit 1400 as shown in FIG. 14A.

Figure 15:
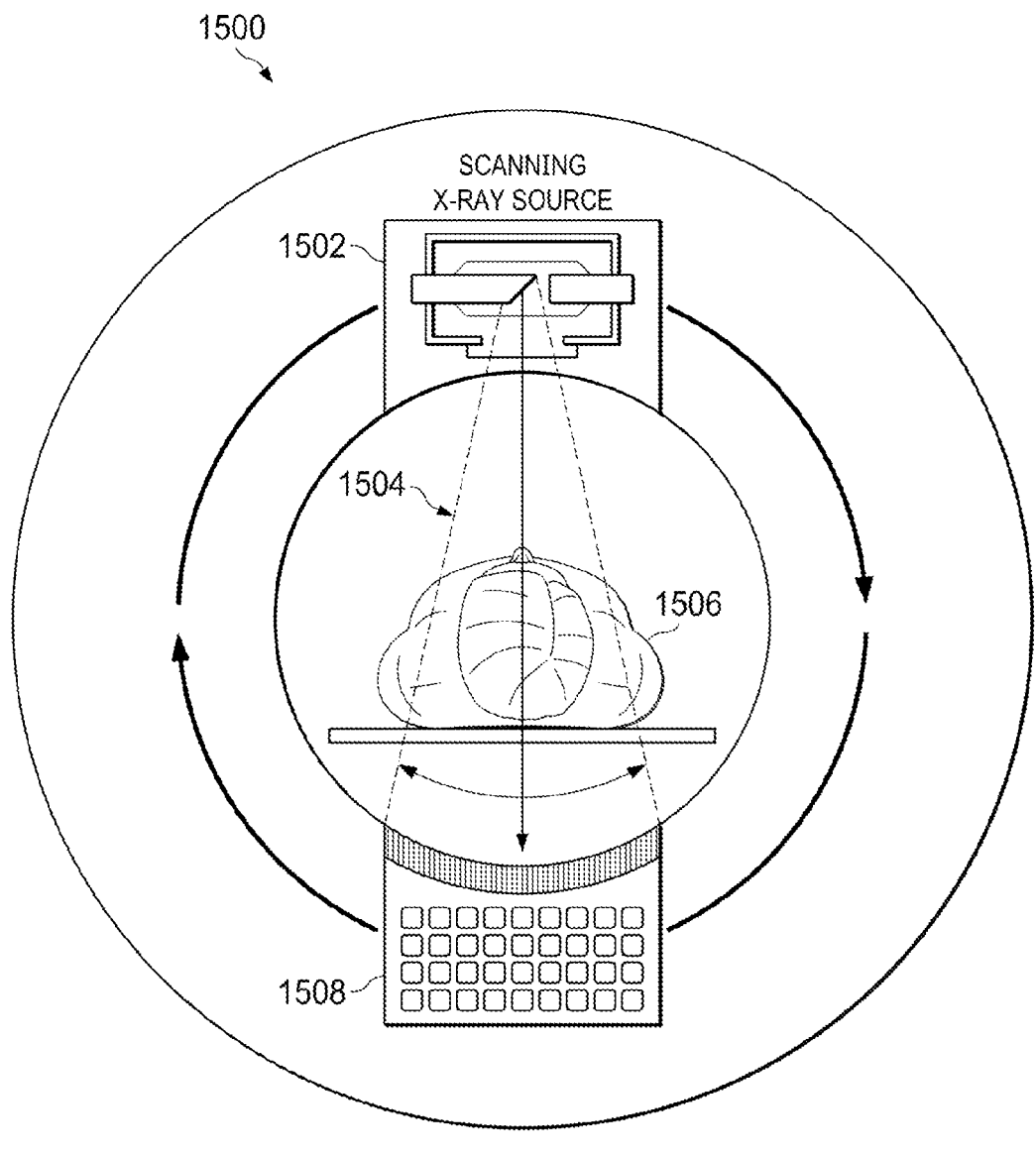
FIG. 15 is a simplified illustration of a PCCT scanning system in accordance with features of certain embodiments described herein.

FIG. 15 illustrates a PCCT 1500 including an X-ray source 1502 that produces X-rays 1504 that are passed through an object of interest 1506 and impinge upon a system 1508, which may be implemented using the system 900 (FIG. 9), for example, including a PCD for converting the received X-rays and processing the converted signals as described herein.

Figure 16:
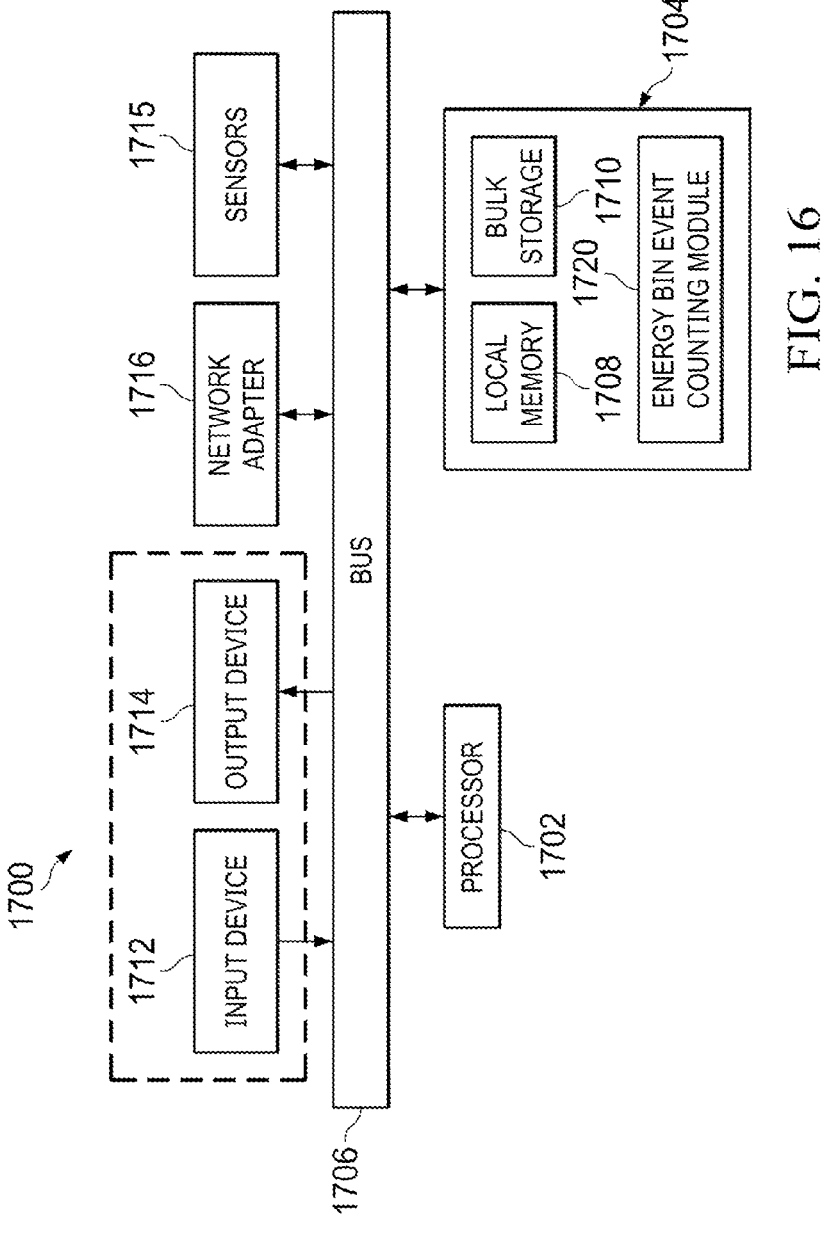
FIG. 16 is a block diagram of a computer system that may be used to implement all or some portion of a photon-counting CT scanning system in accordance with features of certain embodiments described herein.

FIG. 16 is a block diagram illustrating an example system 1700 that may be configured to implement at least portions of techniques in accordance with embodiments described herein, and more particularly as shown in the FIGURES described hereinabove. As shown in FIG. 16, the system 1700 may include at least one processor 1702, e.g. a hardware processor 1702, coupled to memory elements 1704 through a system bus 1706. As such, the system may store program code and/or data within memory elements 1704. Further, the processor 1702 may execute the program code accessed from the memory elements 1704 via a system bus 1706. In one aspect, the system may be implemented as a computer that is suitable for storing and/or executing program code. It should be appreciated, however, that the system 1700 may be implemented in the form of any system including a processor and a memory that is capable of performing the functions described in this disclosure.

In some embodiments, the processor 1702 can execute software or an algorithm to perform the activities as discussed in this specification; in particular, activities related to embodiments described herein. The processor 1702 may include any combination of hardware, software, or firmware providing programmable logic, including by way of non-limiting example a microprocessor, a DSP, a field-programmable gate array (FPGA), a programmable logic array (PLA), an integrated circuit (IC), an application specific IC (ASIC), or a virtual machine processor. The processor 1702 may be communicatively coupled to the memory element 1704, for example in a direct-memory access (DMA) configuration, so that the processor 1702 may read from or write to the memory elements 1704.

In general, the memory elements 1704 may include any suitable volatile or non-volatile memory technology, including double data rate (DDR) random access memory (RAM), synchronous RAM (SRAM), dynamic RAM (DRAM), flash, read-only memory (ROM), optical media, virtual memory regions, magnetic or tape memory, or any other suitable technology. Unless specified otherwise, any of the memory elements discussed herein should be construed as being encompassed within the broad term "memory." The information being measured, processed, tracked or sent to or from any of the components of the system 1700 could be provided in any database, register, control list, cache, or storage structure, all of which can be referenced at any suitable timeframe. Any such storage options may be included within the broad term "memory" as used herein. Similarly, any of the potential processing elements, modules, and machines described herein should be construed as being encompassed within the broad term "processor." Each of the elements shown in the present figures may also include suitable interfaces for receiving, transmitting, and/or otherwise communicating data or information in a network environment so that they can communicate with, for example, a system having hardware similar or identical to another one of these elements.

In certain example implementations, mechanisms for implementing embodiments as outlined herein may be implemented by logic encoded in one or more tangible media, which may be inclusive of non-transitory media, e.g., embedded logic provided in an ASIC, in DSP instructions, software (potentially inclusive of object code and source code) to be executed by a processor, or other similar machine, etc. In some of these instances, memory elements, such as e.g. the memory elements 1704 shown in FIG. 16 can store data or information used for the operations described herein. This includes the memory elements being able to store software, logic, code, or processor instructions that are executed to carry out the activities described herein. A processor can execute any type of instructions associated with the data or information to achieve the operations detailed herein. In one example, the processors, such as e.g. the processor 1702 shown in FIG. 16, could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., an FPGA, a DSP, an erasable programmable read-only memory (EPROM), an electrically erasable programmable read-only memory (EEPROM)) or an ASIC that includes digital logic, software, code, electronic instructions, or any suitable combination thereof.

The memory elements 1704 may include one or more physical memory devices such as, for example, local memory 1708 and one or more bulk storage devices 1170. The local memory may refer to RAM or other non-persistent memory device(s) generally used during actual execution of the program code. A bulk storage device may be implemented as a hard drive or other persistent data storage device. The processing system 1700 may also include one or more cache memories (not shown) that provide temporary storage of at least some program code in order to reduce the number of times program code must be retrieved from the bulk storage device 1170 during execution.

As shown in FIG. 16, the memory elements 1704 may store an energy bin event counting module 1720. In various embodiments, the module 1720 may be stored in the local memory 1708, the one or more bulk storage devices 1170, or apart from the local memory and the bulk storage devices. It should be appreciated that the system 1700 may further execute an operating system (not shown in FIG. 16) that can facilitate execution of the module 1720. The module 1720, being implemented in the form of executable program code and/or data, can be read from, written to, and/or executed by the system 1700, e.g., by the processor 1702. Responsive to reading from, writing to, and/or executing the module 1720, the system 1700 may be configured to perform one or more operations or method steps described herein.

Input/output (I/O) devices depicted as an input device 1712 and an output device 1714, optionally, may be coupled to the system. Examples of input devices may include, but are not limited to, a keyboard, a pointing device such as a mouse, or the like. Examples of output devices may include, but are not limited to, a monitor or a display, speakers, or the like. In some implementations, the system may include a device driver (not shown) for the output device 1714. Input and/or output devices 1712, 1714 may be coupled to the system 1700 either directly or through intervening I/O controllers. Additionally, sensors 1715, may be coupled to the system 1700 either directly or through intervening controllers and/or drivers.

In an embodiment, the input and the output devices may be implemented as a combined input/output device (illustrated in FIG. 16 with a dashed line surrounding the input device 1712 and the output device 1714). An example of such a combined device is a touch sensitive display, also sometimes referred to as a "touch screen display" or simply "touch screen". In such an embodiment, input to the device may be provided by a movement of a physical object, such as e.g. a stylus or a finger of a user, on or near the touch screen display.

A network adapter 1716 may also, optionally, be coupled to the system 1700 to enable it to become coupled to other systems, computer systems, remote network devices, and/or remote storage devices through intervening private or public networks. The network adapter may comprise a data receiver for receiving data that is transmitted by said systems, devices and/or networks to the system 1700, and a data transmitter for transmitting data from the system 1700 to said systems, devices and/or networks. Modems, cable modems, and Ethernet cards are examples of different types of network adapter that may be used with the system 1700.

As previously noted, undershoot occurs when the average of the signal current is high enough that its cancellation by the BLR circuit causes a significant negative shift in the baseline. Although BLR does distort the measured spectrum with undershoot, its benefit in terms of canceling leakage current outweighs the distorting effect. In accordance with features of embodiments described above, a nonlinear BLR circuit that behaves like a delta modulator reduces the effect of large shaper peaks, resulting in less undershoot. The use of a mixed-signal delta modulator enables implementation of a clocked version of the BLR circuit that can achieve a smaller silicon area and cancel amplifier offsets.

Example 1 is a baseline restoration ("BLR") circuit for a photon-counting computed tomography ("PCCT") signal chain, the BLR circuit including an input comparator for comparing a shaper voltage output from a shaper component of the PCCT signal chain with a baseline voltage, the input comparator outputting a single bit indicative of whether the shaper voltage is above or below the baseline voltage; and a low pass filter connected to filter a voltage signal output from the input comparator.

In Example 2, the BLR circuit of Example 1 may further include a transconductor connected to receive a filtered voltage signal output from the low pass filter, convert the filtered voltage signal to a current signal, and feed the current signal back to an input of the PCCT signal chain.

In Example 3, the BLR circuit of any of Examples 1-2 may further include a delta modulator circuit for providing nonlinear BLR.

In Example 4, the BLR circuit of Example 3 may further include the low pass filter comprising an integrator of the delta-modulation circuit.

In Example 5, the BLR circuit of any of Examples 1-4 may further include the BLR circuit comprising a feedback loop that functions as a delta modulator.

In Example 6, the BLR circuit of any of Examples 1-5 may further include the BLR circuit being clocked.

In Example 7, the BLR circuit of any of Examples 1-6 may further include chopper stabilization applied to null out the offset of the input comparator.

In Example 8, the BLR circuit of any of Examples 1-7 may further include an auto-zero technique being applied to null out the offset of the input comparator.

In Example 9, the BLR circuit of any of Examples 1-8 may further include the BLR circuit being clocked and chopper stabilization being applied to null out the offset of the input comparator.

In Example 10, the BLR circuit of any of Examples 1-9 may further include the BLR circuit being clocked and an auto-zero technique being applied to null out the offset of the input comparator.

Example 11 is a method for implementing non-linear baseline restoration ("BLR") in connection with a photo-counting computed tomography ("PCCT") signal chain, the method comprising comparing a shaper voltage output from a shaper component of the PCCT signal chain with a baseline voltage to produce a comparator voltage indicative of whether the shaper voltage is above or below the baseline voltage at a given time; filtering the comparator voltage; and converting the filtered voltage signal to a current signal.

In Example 12, the method of Example 11 may further include feeding the current signal back to an input of the PCCT signal chain.

In Example 13, the method of Example-12 may further include the comparing, filtering, converting, and feeding being performed by a delta-modulation circuit.

In Example 14, the method of any of Examples 11-13 may further include clocking the comparing and filtering.

In Example 15, the method of any of Examples 11-14 may further include applying chopper stabilization to null out an offset of an input comparator of the PCCT signal chain.

In Example 16, the method of any of Examples 11-15 may further include applying an auto-zero technique to null out an offset of an input comparator of the PCCT signal chain.

In Example 17, the method of any of Examples 11-16 may further include clocking the comparing and filtering; and applying chopper stabilization to null out an offset of an input comparator of the PCCT signal chain.

In Example 18, the method of any of Examples 11-17 may further include the filtering being performed using a low pass filter.

In Example 19, the method of any of Examples 11-18 may further include applying a low-duty-cycle clock signal to the low-pass filter to increase a value of a time constant.

Example 20 is a photon-counting detector ("PCD") comprising a sensor for registering an interaction with a photon received at the PCD and forwarding a pulse indicative of the interaction to a signal chain; and a baseline restoration ("BLR") circuit connected to the signal chain, the BLR circuit comprising an input comparator for comparing a voltage pulse output from the signal chain with a baseline voltage, the input comparator outputting a single bit indicative of whether the shaper voltage is above or below the baseline voltage; and a low pass filter connected to filter a voltage signal output from the input comparator.

In Example 21, the PCD of Example 20 may further include the BLR circuit comprising a transconductor connected to receive a filtered voltage signal output from the low pass filter, convert the filtered voltage signal to a current signal, and feed the current signal back to an input of the signal chain.

In Example 22, the PCD of any of Examples 20-21 may further include the BLR circuit comprising a delta modulator circuit for providing nonlinear BLR.

In Example 23, the PCD of any of Examples 20-22 may further include the signal chain comprising a charge sensing amplifier ("CSA") for amplifying the pulse received from the sensor and outputting an amplified pulse; and a pulse shaper ("PS") for shaping the amplified pulse and producing the voltage pulse output from the signal chain.

In Example 24, the PCD of any of Examples 20-23 may further include a counting circuit for categorizing and counting the voltage pulse output from the signal chain.

In Example 25, the PCD of any of Examples 20-24 may further include the BLR circuit comprising a feedback loop that functions as a delta modulator.

In Example 26, the PCD of any of Examples 20-25 may further include the BLR circuit being clocked.

In Example 27, the PCD of any of Examples 20-26 may further include chopper stabilization being applied in the BLR circuit to null out the offset of the input comparator.

In Example 28, the PCD of any of Examples 20-27 may further include an auto-zero technique being applied in the BLR circuit to null out the offset of the input comparator.

In Example 29, the PCD of any of Examples 20-28 may further include the BLR circuit being clocked and chopper stabilization being applied to null out the offset of the input comparator.

Example 30 is a photon-counting computed tomography ("PCCT") system comprising an X-ray source for generating an X-ray photons; and a photon-counting detector ("PCD") comprising a sensor for registering an interaction with an X-ray photon received at the PCD after passing through an object of interest and forwarding a pulse indicative of the interaction to a signal chain; and a baseline restoration ("BLR") circuit connected to the signal chain, the BLR circuit comprising an input comparator for comparing a voltage pulse output from the signal chain with a baseline voltage, the input comparator outputting a single bit indicative of whether the shaper voltage is above or below the baseline voltage and a low pass filter connected to filter a voltage signal output from the input comparator.

In Example 31, wherein the PCCT system of Example 30 further including the BLR circuit further comprising a transconductor connected to receive a filtered voltage signal output from the low pass filter, convert the filtered voltage signal to a current signal, and feed the current signal back to an input of the signal chain.

In Example 32, the PCCT system of any of Examples 30-31 may further include the BLR circuit comprising a delta modulator circuit for providing nonlinear BLR.

In Example 33, the PCCT system of any of Examples 30-32 may further include the signal chain comprising a charge sensing amplifier ("CSA") for amplifying the pulse received from the sensor and outputting an amplified pulse; and a pulse shaper ("PS") for shaping the amplified pulse and producing the voltage pulse output from the signal chain.

In Example 34, the PCCT system of any of Examples 30-33 may further include a counting circuit for categorizing and counting the voltage pulse output from the signal chain.

In Example 35, the PCCT system of any of Examples 30-34 may further include the BLR circuit comprising a feedback loop that functions as a delta modulator.

In Example 36, the PCCT system of any of Examples 30-35 may further include the BLR circuit being clocked.

In Example 37, the PCCT system of any of Examples 30-36 may further include chopper stabilization being applied in the BLR circuit to null out the offset of the input comparator.

In Example 38, the PCCT system of any of Examples 30-37 may further include an auto-zero technique being applied in the BLR circuit to null out the offset of the input comparator.

In Example 39, the PCCT system of any of Examples 30-38 may further include the BLR circuit being clocked and chopper stabilization being applied to null out the offset of the input comparator.

It should be noted that all of the specifications, dimensions, and relationships outlined herein (e.g., the number of elements, operations, steps, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, exemplary embodiments have been described with reference to particular component arrangements. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more electrical components. However, this has been done for purposes of clarity and example only. It should be appreciated that the system may be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the FIGURES and its teachings are readily scalable and may accommodate a large number of components, as well as more complicated/sophisticated arrangements and configurations. Accordingly, the examples provided should not limit the scope or inhibit the broad teachings of the electrical circuits as potentially applied to myriad other architectures.

It should also be noted that in this Specification, references to various features (e.g., elements, structures, modules, components, steps, operations, characteristics, etc.) included in "one embodiment", "exemplary embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It should also be noted that the functions related to circuit architectures illustrate only some of the possible circuit architecture functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

Note that all optional features of the device and system described above may also be implemented with respect to the method or process described herein and specifics in the examples may be used anywhere in one or more embodiments.

The 'means for' in these instances (above) may include (but is not limited to) using any suitable component discussed herein, along with any suitable software, circuitry, hub, computer code, logic, algorithms, hardware, controller, interface, link, bus, communication pathway, etc.

Note that with the example provided above, as well as numerous other examples provided herein, interaction may be described in terms of two, three, or four network elements. However, this has been done for purposes of clarity and example only. In certain cases, it may be easier to describe one or more of the functionalities of a given set of flows by only referencing a limited number of network elements. It should be appreciated that topologies illustrated in and described with reference to the accompanying FIG-URES (and their teachings) are readily scalable and may accommodate a large number of components, as well as more complicated/sophisticated arrangements and configurations. Accordingly, the examples provided should not limit the scope or inhibit the broad teachings of the illustrated topologies as potentially applied to myriad other architectures.

It is also important to note that the steps in the preceding flow diagrams illustrate only some of the possible signaling scenarios and patterns that may be executed by, or within, communication systems shown in the FIGURES. Some of these steps may be deleted or removed where appropriate, or these steps may be modified or changed considerably without departing from the scope of the present disclosure. In addition, a number of these operations have been described as being executed concurrently with, or in parallel to, one or more additional operations. However, the timing of these operations may be altered considerably. The preceding operational flows have been offered for purposes of example and discussion. Substantial flexibility is provided by communication systems shown in the FIGURES in that any suitable arrangements, chronologies, configurations, and timing mechanisms may be provided without departing from the teachings of the present disclosure.

Although the present disclosure has been described in detail with reference to particular arrangements and configurations, these example configurations and arrangements may be changed significantly without departing from the scope of the present disclosure. For example, although the present disclosure has been described with reference to particular communication exchanges, embodiments described herein may be applicable to other architectures.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 142 as it exists on the date of the filing hereof unless the words "means for" or "step for" are specifically used in the particular claims; and (b) does not intend, by any statement in the specification, to limit this disclosure in any way that is not otherwise reflected in the appended claims.

The invention claimed is:

1. A baseline restoration ("BLR") circuit for a photon-counting computed tomography ("PCCT") signal chain, the BLR circuit comprising:

an input comparator for comparing a shaper voltage output from a shaper component of the PCCT signal chain with a baseline voltage, the input comparator outputting a single bit indicative of whether the shaper voltage is above or below the baseline voltage; and
a low pass filter connected to filter a voltage signal output from the input comparator.

2. The BLR circuit of claim 1, further comprising a transconductor connected to receive a filtered voltage signal output from the low pass filter, convert the filtered voltage signal to a current signal, and feed the current signal back to an input of the PCCT signal chain.

3. The BLR circuit of claim 1, comprising a delta modulator circuit for providing nonlinear BLR.

4. The BLR circuit of claim 3, wherein the low pass filter comprises an integrator of the delta modulator circuit.

5. The BLR circuit of claim 1, further comprising a feedback loop that functions as a delta modulator.

6. The BLR circuit of claim 1, wherein the BLR circuit is clocked.

7. The BLR circuit of claim 1, wherein chopper stabilization is applied to null out an offset of the input comparator.

8. The BLR circuit of claim 1, wherein an auto-zero technique is applied to null out an offset of the input comparator.

9. The BLR circuit of claim 1, wherein the BLR circuit is clocked and chopper stabilization is applied to null out an offset of the input comparator.

10. The BLR circuit of claim 1, wherein the BLR circuit is clocked and an auto-zero technique is applied to null out an offset of the input comparator.

11. The BLR circuit of claim 1, wherein the low pass filter is in a non-feedback configuration.

12. A method for implementing non-linear baseline restoration ("BLR"), the method comprising:

comparing a shaper voltage output from a shaper component of a photon-counting computed tomography (PCCT) signal chain with a baseline voltage to produce a comparator voltage indicative of whether the shaper voltage is above or below the baseline voltage at a given time;
filtering the comparator voltage; and
converting the filtered voltage signal to a current signal.

13. The method of claim 12, further comprising feeding the current signal back to an input of the PCCT signal chain.

14. The method of claim 13, wherein the comparing, filtering, converting, and feeding is performed by a delta-modulation circuit.

15. The method of claim 12, further comprising clocking the comparing and filtering.

16. The method of claim 12, further comprising applying chopper stabilization to null out an offset of an input comparator of the PCCT signal chain.

17. The method of claim 12, further comprising applying an auto-zero technique to null out an offset of an input comparator of the PCCT signal chain.

18. The method of claim 12, further comprising:
clocking the comparing and filtering; and
applying chopper stabilization to null out an offset of an input comparator of the PCCT signal chain.

19. The method of claim 12, wherein the filtering is performed using a low-pass filter.

20. The method of claim 19, further comprising applying a low-duty-cycle clock signal to the low-pass filter to increase a value of a time constant.

* * * * *